US011759562B2

(12) United States Patent
Radwanski et al.

(10) Patent No.: US 11,759,562 B2
(45) Date of Patent: Sep. 19, 2023

(54) LOW VOLUME EXTRACORPOREAL PHOTOPHERESIS SYSTEMS AND METHODS

(71) Applicant: Fenwal, Inc., Lake Zurich, IL (US)

(72) Inventors: Katherine N. Radwanski, Highland Park, IL (US); Jonathan W. Prendergast, Palatine, IL (US)

(73) Assignee: Fenwal Inc., Lake Zurich, IL (US)

( * ) Notice: Subject to any disclaimer, the term of this patent is extended or adjusted under 35 U.S.C. 154(b) by 345 days.

(21) Appl. No.: 16/761,923

(22) PCT Filed: Nov. 22, 2019

(86) PCT No.: PCT/US2019/062730
§ 371 (c)(1),
(2) Date: May 6, 2020

(87) PCT Pub. No.: WO2020/139495
PCT Pub. Date: Jul. 2, 2020

(65) Prior Publication Data
US 2021/0154390 A1    May 27, 2021

Related U.S. Application Data

(60) Provisional application No. 62/784,905, filed on Dec. 26, 2018.

(51) Int. Cl.
*A61M 1/36* (2006.01)
(52) U.S. Cl.
CPC ........ *A61M 1/3683* (2014.02); *A61M 1/3693* (2013.01); *A61M 2202/0415* (2013.01); *A61M 2202/0429* (2013.01)

(58) Field of Classification Search
CPC .............. A61M 1/3683; A61M 1/3693; A61M 2202/0415; A61M 2202/0429; A61M 2202/0427; A61M 2202/0439
USPC ........................................................ 356/310
See application file for complete search history.

(56) References Cited

U.S. PATENT DOCUMENTS

| | | |
|---|---|---|
| 5,370,802 A | 12/1994 | Brown |
| 5,523,004 A | 6/1996 | Tanokura et al. |
| 7,433,030 B2 | 10/2008 | Waldo et al. |
| 2002/0091057 A1 | 7/2002 | Westberg et al. |
| 2006/0155236 A1 | 7/2006 | Gara et al. |
| 2007/0100272 A1 | 5/2007 | Briggs |
| 2007/0179423 A1 | 8/2007 | Felt et al. |
| 2011/0136645 A1 | 6/2011 | Ellingboe et al. |
| 2014/0066281 A1 | 3/2014 | Weasler et al. |
| 2014/0234828 A1 | 8/2014 | Pobitschka |
| 2016/0296691 A1 | 10/2016 | Min et al. |

(Continued)

OTHER PUBLICATIONS

International Search Report and Written Opinion, counterpart International Appl. No PCT/US2019/062730, (dated Mar. 3, 2020) (19 pages).

(Continued)

*Primary Examiner* — Md M Rahman
(74) *Attorney, Agent, or Firm* — Cook Alex ltd.

(57) ABSTRACT

Systems and methods for performing low volume (e.g., 500 mL or less) extracorporeal photopheresis (ECP) procedures are disclosed. Each of the different systems and methods eliminates the need for multiple kits and solutions and reduce some of the potential risks inherent in the use of such multiple kits and solutions.

24 Claims, 24 Drawing Sheets

(56) References Cited

U.S. PATENT DOCUMENTS

2016/0317727 A1 11/2016 Hirabuki et al.
2018/0078694 A1 3/2018 Abedin et al.

OTHER PUBLICATIONS

Extended European Search Report for European Application 19903632.8 dated Jul. 22, 2022.

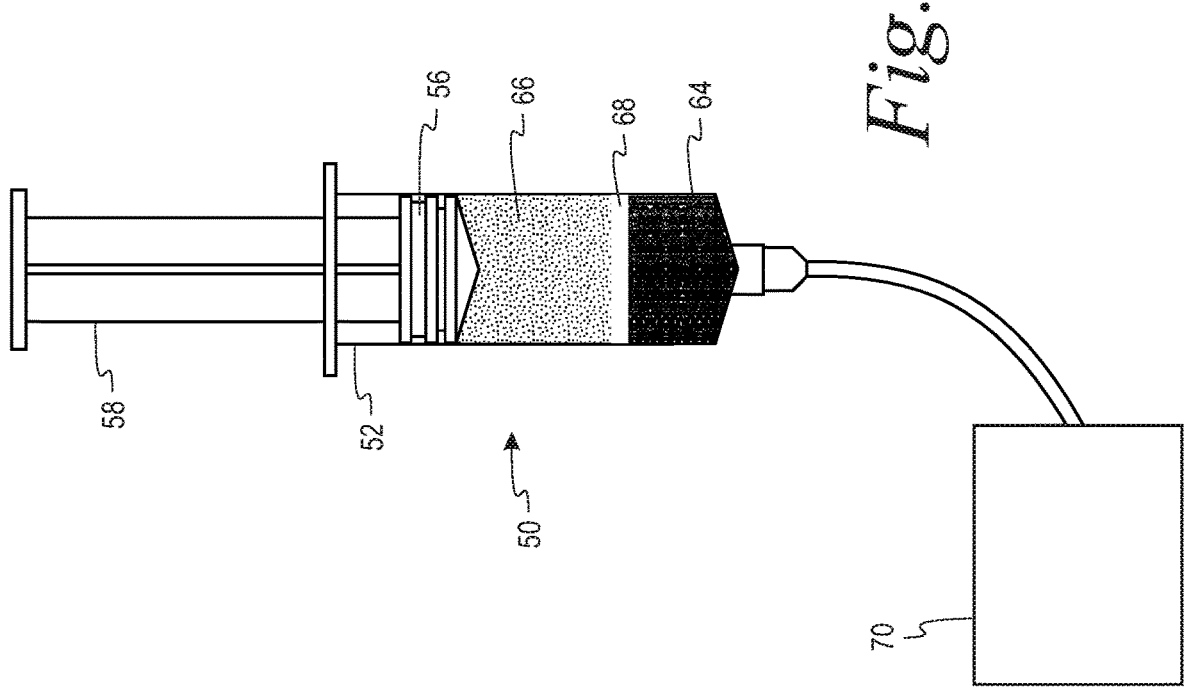
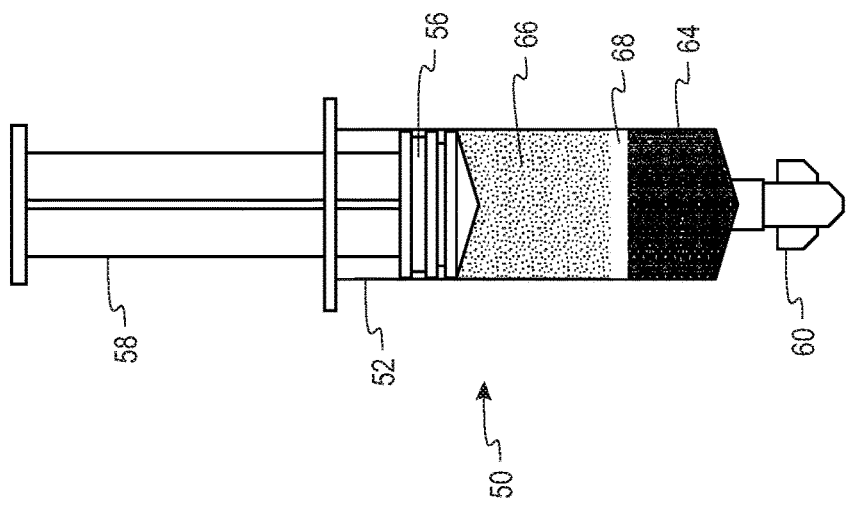

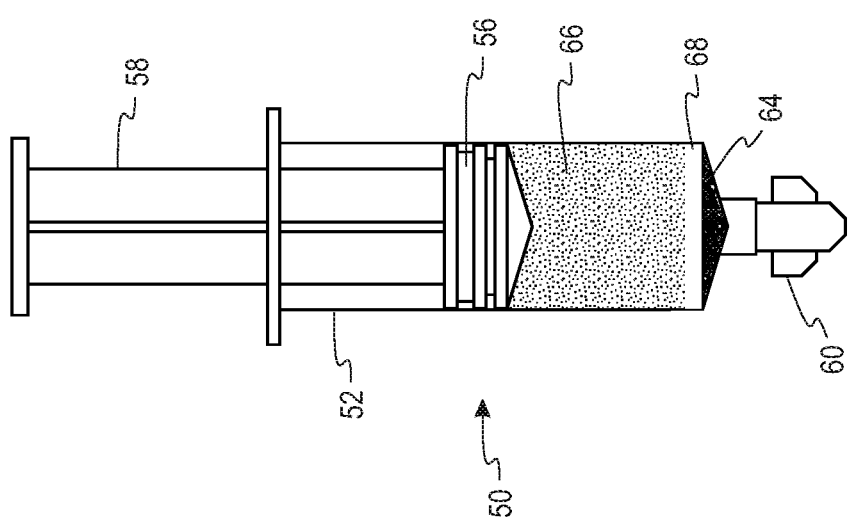

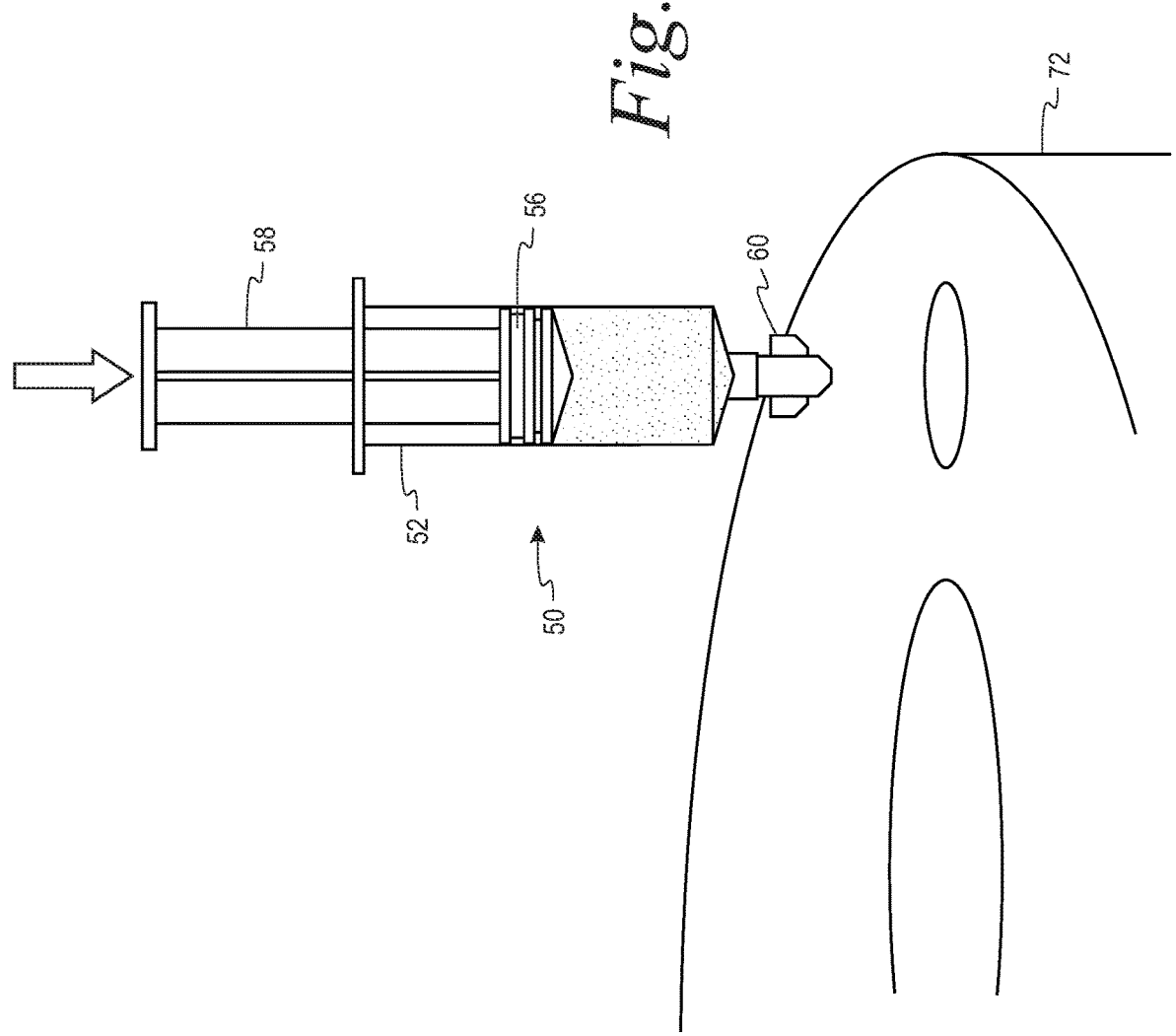

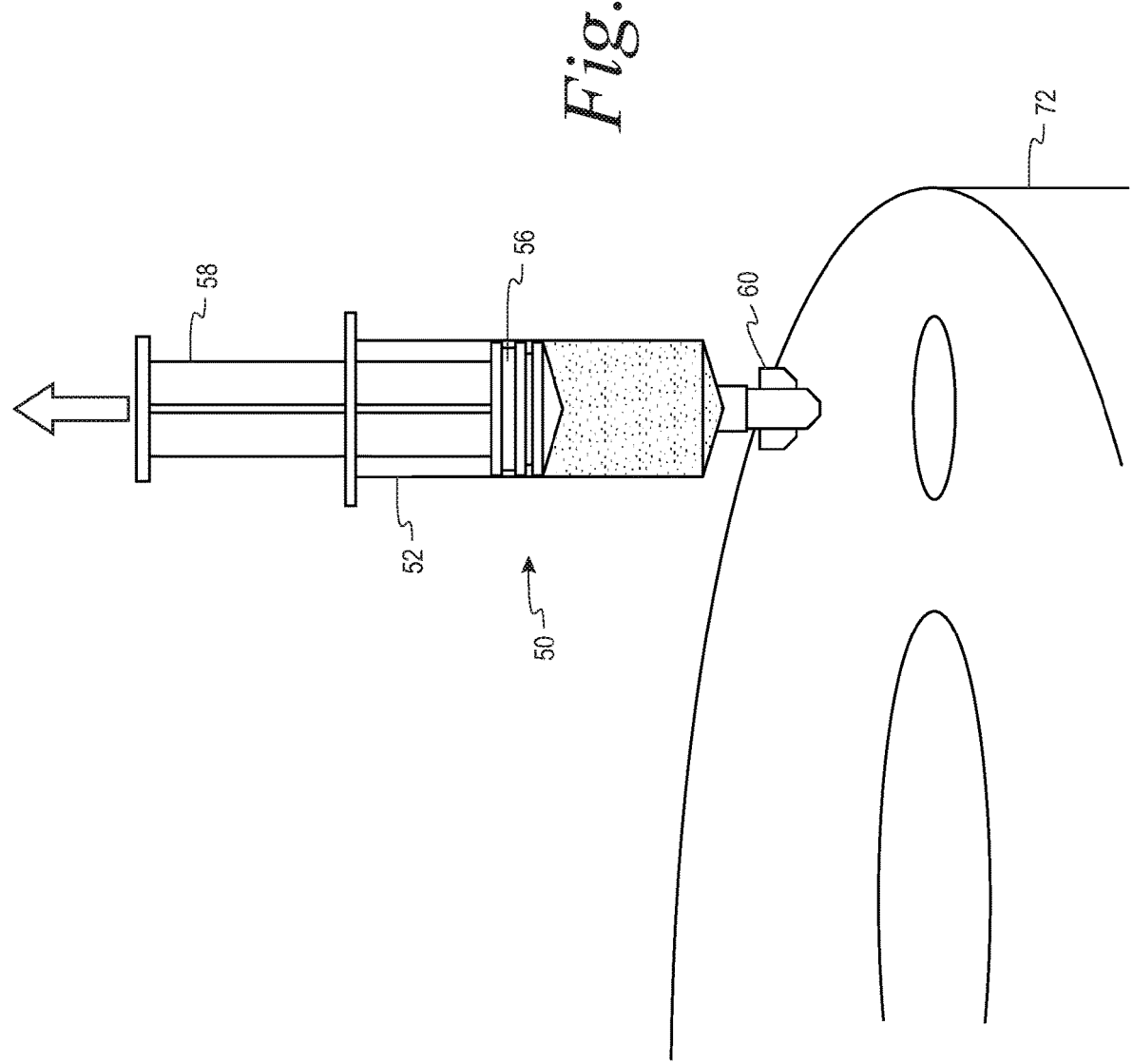

LOW VOLUME EXTRACORPOREAL PHOTOPHERESIS SYSTEMS AND METHODS

Light irradiation therapy is used for the treatment of various blood diseases to, e.g., eliminate immunogenicity in cells, inactivate or kill selected cells, inactivate viruses or bacteria, or activate desirable immune responses. For example, it is known to use the photoactivatable drug psoralen to treat pathogenic blood cells, such as lymphocytes, in an extracorporeal photopheresis (ECP) procedure in which blood is withdrawn from the patient, 8-methoxypsoralen (8-MOP) is added, the white blood cells are separated (typically by centrifugation), and subjected to UV light to activate the 8-MOP molecules. The photoactivated 8-MOP alters the DNA of the pathogenic leukocytes, and the fluid with the altered leukocytes is reinfused back into the patient to induce an immune system response.

ECP typically involves processing a large volume of whole blood, ranging from 1.5 L to 12 L per treatment based on the number of white blood cells collected. Consequently, ECP has proven more difficult to administer to patients that are small in stature, such as pediatric patients, due to their lower body weight, the limits on the extracorporeal volume of the whole blood withdrawn and accompanying fluid balances that may be safely tolerated by such patients, and the relatively large extracorporeal volumes required for operation of apheresis devices used for separating out the white blood cells from the whole blood. Similarly, some adult patients may not be able to tolerate large changes in fluid balance due to their disease state, or have poor venous access, that make ECP procedures difficult to administer.

Set forth in greater detail below are a number of different embodiments of systems and methods specifically developed for performing low volume (e.g., 500 mL or less) ECP procedures. Each of the different systems and methods eliminates the need for multiple kits and solutions and reduce some of the potential risks inherent in the use of such multiple kits and solutions.

SUMMARY

The present disclosure includes five aspects, each having related sub-aspects.

In a first aspect, a unitary disposable kit for performing low volume extracorporeal photopheresis is provided. The kit comprises a first container that is configured to receive whole blood from a patient and to be mountable in both a centrifuge and a blood component separator. A second container is provided that is connected to the upper portion of the first container by a first tubing segment for receipt of plasma. Both the first container and second container have an upper portion and a lower portion when mounted in the centrifuge and blood component separator. A third container is provided that is connected to the lower end of the first container by a second tubing segment for receipt of packed red blood cells. Optionally, the third container may be prefilled with a volume of allogenic, ABO packed red blood cells matched to the patient. A fourth container is provided that is connected to the first container by a third tubing segment for receipt of buffy coat and is also configured to be mountable in an irradiation device. Preferably, each of the first, second, third, and fourth containers is configured to be mountable in the centrifuge.

Related to the first aspect, the unitary disposable kit further may further comprise a phlebotomy needle connected to the first container by a fourth tubing segment for introducing whole blood into the first container and wherein the first container is prefilled with a volume of anticoagulant.

Also related to the first aspect, the unitary disposable kit may further comprise a fifth tubing segment connected to the fourth container for introducing a photoactivation agent into the fourth container. Further, the unitary disposable to kit may comprise a fifth container prefilled with a volume of photoactivation agent and connected to the fourth container by the fifth tubing segment.

In another aspect related to the first aspect, the unitary disposable kit may further comprise a sixth container prefilled with a volume of saline and connected to the first container by a sixth tubing segment for introducing saline into the first container.

Other variations comprise one or more of any of a flow control clamp, a break-away cannula is associated with at least one of the tubing segments, and an in-line antimicrobial filter associated with the fifth tubing segment.

In another aspect related to the first aspect, a method for performing a low volume extracorporeal photopheresis procedure utilizing the unitary disposable kit of the first aspect and the aspects related thereto in combination with a centrifuge, a blood separation device and an irradiation device. the method comprises: mounting a first container containing whole blood in the centrifuge; operating the centrifuge to separate the whole blood into separate layers of plasma at the upper end of the first container, packed red blood cells at the lower end of the first container, and buffy coat intermediate the layers of plasma and packed red blood cells; loading the first container onto the blood separation device; expressing plasma from the upper end of the first container through the first tubing segment and into the second container; expressing packed red blood cells from the lower end of the first container through the second tubing segment and into the third container; retaining the buffy coat in the first container; adding plasma from the second container and/or saline to the first container to dilute the buffy coat retained in the first container and to achieve a target hematocrit and volume for the diluted buffy coat; flowing the diluted buffy coat through the third tubing segment and into the fourth container; adding photoactivation agent to the diluted buffy coat; loading the fourth container onto the irradiation device; and irradiating the fourth container.

In a related aspect, photoactivation agent may be added to the diluted buffy coat by flowing photoactivation agent from the fifth container through the fifth tubing segment and into the fourth container.

In a further related aspect, photoactivation agent may be added to the diluted buffy coat by introducing photoactivation agent into the third tubing segment simultaneously with flowing the diluted buffy coat through the third tubing segment and into the fourth container.

In another related aspect, the buffy coat may diluted by flowing saline from the sixth container through the sixth tubing segment and into the first container.

In another related aspect, the irradiated buffy coat is recombined with a portion of the separated plasma and/or packed red blood cells.

In another related aspect, any excess air in the fourth container is flowed into the first container prior to irradiation of the fourth container.

In another related aspect, a label identifying the patient is applied to at least the fourth container prior to collecting whole blood in the first container and separating the fourth container from the unitary kit only after the diluted buffy coat is flowed from the first container into the fourth container. Optionally, the label identifying the patient is applied to at least the fourth container prior to collecting whole blood in the first container and separating the fourth container from the unitary kit only after the fourth container is irradiated.

In a second aspect, a method for performing low volume extracorporeal photopheresis with a syringe having a needle, a barrel transparent to UVA light; and a stopper slidably received in the barrel having a plunger removably secured thereto in which the syringe contains a volume of whole blood. In the method, the operator performs the steps of: removing the needle from the syringe and attaching a tip cap to the syringe; removing the plunger from the stopper; placing the syringe in a centrifuge; spinning the centrifuge to separate the whole blood into layers comprising red blood cells, plasma and buffy coat; removing the syringe form the centrifuge; reattaching the plunger to the stopper; removing the tip cap and connecting a return container to the syringe; evacuating the layer of red blood cells from the syringe into the return container, leaving only the layer of buffy coat and plasma in the syringe; disconnecting the return container from the syringe and reattaching the tip cap to the syringe; resuspending the buffy coat remaining in the syringe; placing the syringe with the resuspended buffy coat in a UVA irradiation device; irradiating the resuspended buffy coat with UVA light; removing the syringe from the irradiation device; removing the tip cap from the syringe and reattaching the return container to the syringe; and dispensing the entire contents of the syringe into the return container.

In a further aspect related to the second aspect, the method of may further comprise withdrawing whole blood from a patient into the syringe prior to removing the needle from the syringe, and/or infusing the contents of the return container into the patient after dispensing the entire contents of the return container into the patient.

In a further aspect related to the second aspect, the method may include the steps of pre-filling the syringe with a pre-determined volume of photoactivation agent or drawing a pre-determined volume of photoactivation agent into the syringe after removing the needle from the syringe and attaching a tip cap.

In another aspect related to the second aspect, the method may include evacuating the layer of red blood cell from the syringe using an optical scanning device to identify an interface between the layers of red blood cells and buffy coat. Alternatively, the method may comprise evacuating the layer of red blood cells from the syringe with the operator making a visual determination to identify an interface between the layers of red blood cells and buffy coat.

In another aspect related to the second aspect, the method may further comprise drawing air and/or a diluent into the syringe prior to resuspending the buffy coat remaining in the syringe.

In another aspect related to the second aspect, the buffy coat remaining in the syringe is resuspended by means of the operator shaking the syringe. Alternatively, the buffy coat remaining in the syringe is resuspended by means of the operator loading the syringe in to a mechanical shaker and activating the shaker.

In a third aspect, a system for performing extracorporeal photopheresis including a single use disposable fluid flow circuit and a reusable hardware component. The disposable single-use fluid flow circuit comprises: a separation chamber; a first tubing segment in fluid communication with the separation chamber for flowing whole blood from a patient or blood source and into the separation chamber; a second tubing segment in fluid communication with the separation chamber for flowing separated plasma and red blood cells from the separation chamber and to the patient or to a separate container for later reinfusion to the patient; a third tubing segment in fluid communication with the separation chamber for flowing separated, UV-treated MNCs from the separation chamber and to the patient or to the separate container for later reinfusion to the patient; a source of anticoagulant in fluid communication with the first tubing segment through a fourth tubing segment; and a source of photoactivation agent in fluid communication with the first tubing segment through a fifth tubing segment.

The reusable hardware component comprises: a housing; a centrifuge mounted within the housing having a UV-A transmissive bowl configured to mount the separation chamber of the fluid flow circuit therein; a UV-A emitting light source mounted in the housing configured to deliver UV-A light to the bowl of the centrifuge; an interface detector associated with the second tubing segment of the fluid flow circuit configured to detect an interface between separated plasma, red blood cells and MNCs; a first pump associated with the first tubing segment for flowing whole blood from the patient through the first tubing segment and into the separation chamber; a second pump associated with the second tubing segment for flowing separated plasma and red blood cells from the separation chamber through the second tubing segment and back to the patient or to the separate container for later reinfusion to the patient; a third pump associated with the fourth tubing segment for flowing anticoagulant through the forth tubing segment and into the first tubing segment; a fourth pump associated with the fifth tubing segment for flowing photoactivation agent through the fifth tubing segment and into the first tubing segment; and a programmable controller programmed to automatically operate the first, second, third and fourth pumps, the centrifuge, and the UV-A emitting light source.

In a further aspect related to the third aspect, the controller is further programmed to control operation of the second pump based upon a signal received from the interface detector.

In another aspect related to the third aspect, a method for performing extracorporeal photopheresis using the system of the third aspect is provided comprising: introducing whole blood from a patient or a blood source into the first tubing segment; introducing anticoagulant and photoactivation agent into the first tubing segment to mix with the whole blood; flowing the mixture of whole blood, anticoagulant and photoactivation agent from the first tubing segment into the separation chamber; activating the centrifuge to separate the whole blood in the separation chamber into a first layer comprising plasma, a second layer comprising red blood cells, and a third layer comprising MNCs; controlling the centrifuge to flow the plasma and red blood cells out of the separation chamber and into the second tubing segment and to retain the MNCs in the separation chamber; returning the separated plasma and red blood cells to the patient or to the separate container for later reinfusion to the patient; activating the UV-A emitting light source to provide a prescribe dose of UV-A light to the MNCs retained in the separation chamber; operating the centrifuge to flow UV-A treated MNCs from the separation chamber into the third tubing segment; and flowing the UV-A treated MNCs from the third tubing segment back to the patient or to the separate container for later reinfusion to the patient.

In a fourth aspect; a single-use disposable kit for performing low volume extracorporeal photopheresis is provided that comprises: a first container holding photoactivation agent having a first tubing segment connected thereto;

a second container holding saline having a second tubing segment connected thereto; a third tubing segment having a first portion and a second portion, the first portion in fluid communication with both the first tubing segment and the second tubing segment; a mixing container having a fourth tubing segment connected thereto in fluid communication with the first portion of the third tubing segment, a fifth tubing segment connected thereto in fluid communication with the second portion of the third tubing segment, and a sixth tubing segment connected thereto; an irradiation container in fluid communication with the mixing container through the sixth tubing segment and having a seventh tubing segment connected thereto in fluid communication with the second portion of the third tubing segment; and an eighth tubing segment in fluid communication with the irradiation contai In an aspect related to the fourth aspect, the mixing container is pre-filled with whole blood.

In a further aspect related to the fourth aspect, a patient access device is connected to the eighth tubing segment.

In a further aspect related to the fourth aspect, a treated product container is connected to the eighth tubing segment.

In a further aspect related to the fourth aspect, the irradiation container further comprises a fan-shaped cartridge.

In a further aspect related to the fourth aspect, the single-use disposable kit further comprises a container of whole blood having a ninth tubing segment connected thereto, a tenth tubing segment in fluid communication with both the first portion of the third tubing segment and the ninth tubing segment, and an eleventh tubing segment in fluid communication with both the second portion of the third tubing segment and the ninth tubing segment.

In a further aspect related to the fourth aspect, a system for performing low volume extracorporeal photopheresis is provided that comprises the single-use disposable kit of the fourth aspect, as set forth above, and a reusable hardware component to which the single-use disposable kit is mounted. The reusable hardware component comprises one or more of: a first fluid flow control device associated with the first tubing segment; a second fluid flow control device associated with the second tubing segment; a third fluid flow control device associated with the third tubing segment; a fourth fluid flow control device associated with the fourth tubing segment; a fifth fluid flow control device associated with the fifth tubing segment; a sixth fluid flow control associated with the sixth tubing segment; a seventh fluid flow control device associated with the seventh tubing segment; and an eighth fluid flow control device associated with the eighth tubing segment. The hardware component further comprises: an agitation device configured to receive the mixing container; an irradiation device having a UV light source configured to receive the irradiation container; and a programmable controller for automatically operating the fluid flow control devices, the agitation device and the irradiation device.

In a further aspect of the fourth aspect, the third fluid flow control device of the system comprises a pump interposed between the first and second portions of the third tubing segment.

In a further aspect of the fourth aspect, each of the first, second, fourth, fifth, sixth, seventh, and eighth fluid flow control devices of the system comprises a valve or a clamp.

In a further aspect related to the fourth aspect, a system for performing low volume extracorporeal photopheresis is provided that comprises the single-use disposable kit of the fourth aspect, as set forth above, in which the single-use disposable kit further comprises a container of whole blood having a ninth tubing segment connected thereto, a tenth tubing segment in fluid communication with both the first portion of the third tubing segment and the ninth tubing segment, and an eleventh tubing segment in fluid communication with both the second portion of the third tubing segment and the ninth tubing segment, and a reusable hardware component to which the single-use disposable kit is mounted. The reusable hardware component comprises one or more of: a first fluid flow control device associated with the first tubing segment; a second fluid flow control device associated with the second tubing segment; a third fluid flow control device associated with the third tubing segment; a fourth fluid flow control device associated with the fourth tubing segment; a fifth fluid flow control device associated with the fifth tubing segment; a sixth fluid flow control associated with the sixth tubing segment; a seventh fluid flow control device associated with the seventh tubing segment; an eighth fluid flow control device associated with the eighth tubing segment; a ninth fluid flow control device associated with the ninth tubing segment; an agitation device for receiving the mixing container; an irradiation device having a UV light source for receiving the irradiation container; and a programmable controller for automatically operating the fluid flow control devices, the agitation device and the irradiation device. The third fluid flow control device may comprise a pump interposed between the first and second portions of the third tubing segment, and each of the first, second, fourth, fifth, sixth, seventh, eighth and ninth fluid flow control devices may comprise a valve or a clamp.

In a fifth aspect, a single-use fluid flow circuit for performing low volume extracorporeal photopheresis is provided, comprising: a separation chamber configured to be received in a centrifuge; a first tubing segment connected to the separation chamber for flowing whole blood thereto; a collection container for receipt of buffy coat separated from the whole blood in the separation chamber by operation of the centrifuge and configured to be received in a treatment chamber of an irradiation device; and a second tubing segment for flowing buffy coat from the separation chamber onto the collection container.

In a further aspect related to the fifth aspect, the fluid flow circuit further comprises a container of photoactivation agent connected to the collection container.

In another aspect related to the fifth aspect, the collection container of the fluid flow circuit comprises a syringe.

In a still further aspect related to the fifth aspect, the first tubing segment comprises one of a phlebotomy device for flowing whole blood directly from a patient through the first tubing segment and to the separation chamber and a sterile connector for connecting a container of previously-collected whole blood to the first tubing segment.

In another aspect related to the fifth aspect, a system for performing low volume extracorporeal photopheresis comprising the single-use fluid flow circuit of the fifth aspect and a durable hardware component. The durable hardware component further comprises a centrifuge configured to receive the separation chamber of the fluid flow circuit; one or more pumps for flowing whole blood through the first tubing segment to the separation chamber and flowing buffy coat through the second tubing segment into the collection container; an irradiation device having a treatment chamber configured to receive the collection container, and a programmable controller for automatically operating the one or more pumps, the centrifuge and the irradiation device. In a further embodiment, the one or more pumps are associated with each of the first and second tubing segments.

BRIEF DESCRIPTION OF DRAWINGS

FIGS. 2-16 illustrate the steps of a second method for performing a low volume ECP procedure that utilizes a syringe-like container.

DESCRIPTION OF THE ILLUSTRATED EMBODIMENTS

The embodiments disclosed herein are for the purpose of providing and exemplary description of the present subject matter. They are, however, only exemplary, and the present subject matter may be embodied in various forms. Therefore, specific details disclosed herein are not to be interpreted as limiting the subject matter defined in the accompanying claims.

Figure 1:
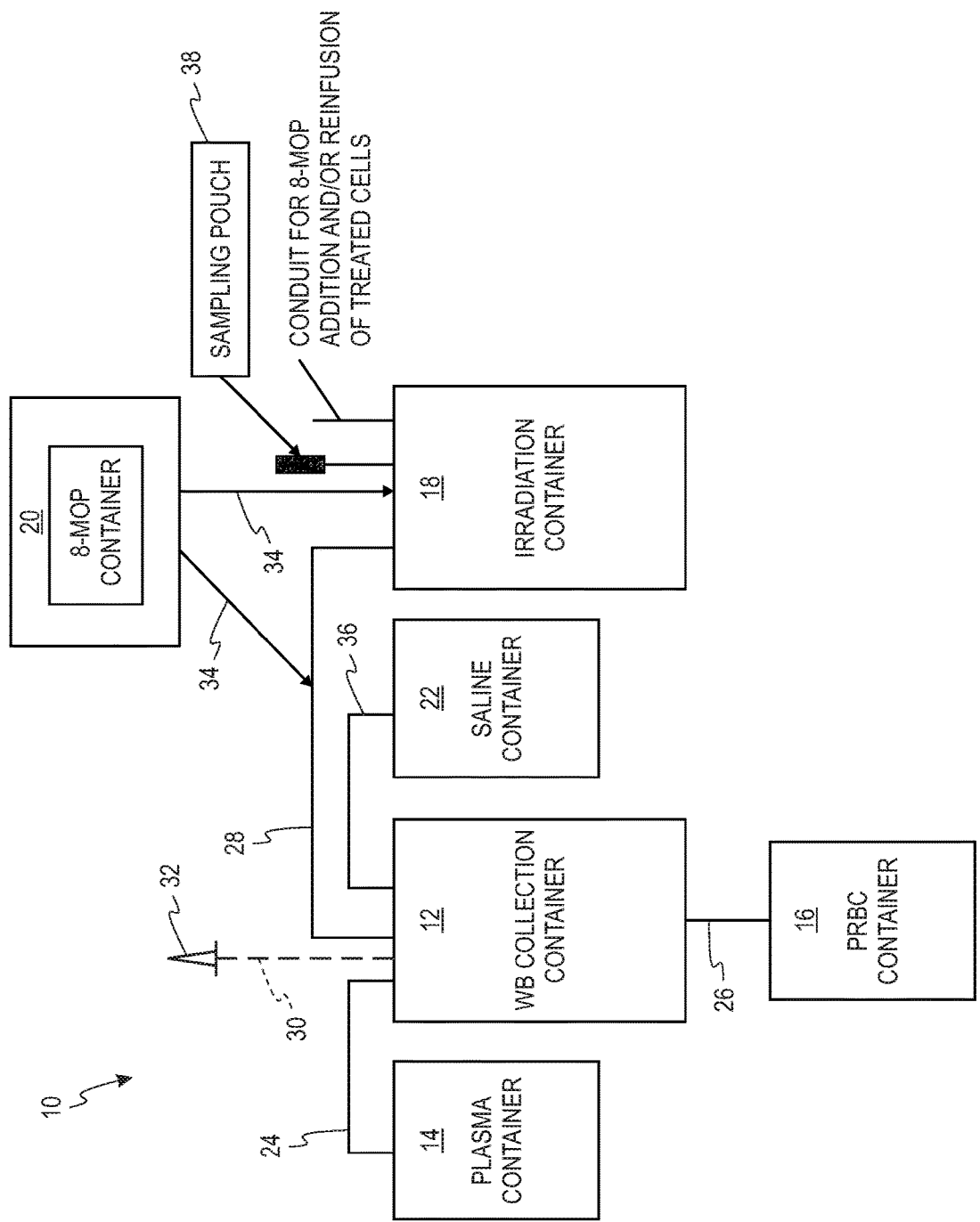
FIG. 1 is a schematic drawing of a disposable fluid flow circuit usable in a first method for performing a low volume ECP procedure.

In a first aspect and with reference to FIG. 1, an all-in-one disposable fluid flow circuit or kit for performing a low volume ECP procedure generally designated 10 is disclosed. The kit includes a number of different containers that are interconnected by tubing segments. More particularly, the kit 10 includes a first container 12 into which a volume of whole blood is collected. The whole blood collection container 12 is optionally pre-filled with a volume of anticoagulant, if anticoagulant was not added to the whole blood upon withdrawing it from the patient. The whole blood collection container 12 also serves as the separation chamber, and is thus configured to be received in the bowl of a centrifuge used for separating the components of the whole blood. Typically, separation is performed in a large, floor-standing, high capacity blood banking centrifuge, such as the Sorvall™ centrifuge available from Thermo Fisher Scientific Inc. Alternatively, an apheresis centrifuge may be used, such as the Amicus® Separator, available from Fenwal, Inc., the details of which may be found in, e.g., U.S. Pat. No. 5,370,802.

The kit further includes a second collection container 14 and a third collection container 16 for the plasma and packed red blood cells, respectively, separated out from the whole blood during centrifugation. In instances where the patient is not able to donate a full unit of whole blood, the collection container 16 for the packed red blood cells may contain a volume of allogenic, ABO-matched red blood cells, which can be added to the whole blood collection container 12 prior to buffy coat separation. A fourth collection container 18 which serves as an irradiation container is provided into which the buffy coat remaining in the whole blood collection container 12 is transferred. The irradiation container 18 is configured to be received in the treatment chamber of an irradiation device. An exemplary irradiation device is described in U.S. Pat. No. 7,433,030. The kit also optionally includes pre-attached fifth and sixth containers 20, 22 of photoactivation agent (8-MOP) and saline, respectively.

Tubing segments interconnect the various containers. Specifically, a first tubing segment 24 connects the plasma collection container 14 to the upper end of the whole blood collection container/separation chamber 12. A second tubing segment 26 connects the lower end of the whole blood collection container/separation chamber 12 to the red blood cell collection container 16. A third tubing segment 28 connects the whole blood collection container/separation chamber 12 to the irradiation container 18. Optionally, a fourth tubing segment 30 having a phlebotomy needle 32 on the end thereof may be connected to the whole blood collection container/separation chamber 12 for introducing whole blood into the whole blood collection container/separation chamber 12. A fifth tubing segment 34 is connected to the irradiation container 18 for introducing photoactivation agent from the container 20 of photoactivation agent into the irradiation container. The tubing segment 34 may connect the container 20 directly to the irradiation container, or may connect the container 20 to tubing segment 28. A sixth tubing segment 36 connects the saline container 22 to the whole blood collection container/separation chamber 12.

Variations of the kit 10 include providing the tubing segments interconnecting the containers with means for controlling the flow between the containers, such as clamps, valves, and/or break-away cannulas. Further, a sampling pouch 38 may be connected to the irradiation container.

The fluid flow circuit/kit may 10 be used in the following manner. First, whole blood is collected into the whole blood collection container 12. The whole blood collection container 12 is then loaded into the bowl of a centrifuge, and the entire kit 10 is centrifuged to separate the whole blood into plasma, buffy coat and packed red blood cell layers.

The kit 10 is removed from the centrifuge and loaded onto an automated separation device, such as the CompoMat® G5 automated blood component separator available from Fresenius Kabi, which expresses the plasma layer into the plasma collection container 14 and the packed red blood cells to the packed red blood cell collection container 16, while the buffy coat is retained in the whole blood collection container 12. A target hematocrit and volume of the buffy coat required for irradiation is achieved by adding some of the separated plasma back into the whole blood collection container 12 and/or adding saline to the whole blood collection container 12.

The diluted buffy coat is then transferred (by, e.g., draining or gravity feed) into the irradiation container 18. The photoactivation agent (8-MOP) may be added in line with the transfer of the diluted buffy coat into the irradiation container. Alternatively, the photoactivation agent may be added directly to the irradiation container. Any excess air in the irradiation container 18 after the introduction of the diluted buffy coat and photoactivation agent may be flowed back into the whole blood collection container 12 by burping the irradiation container 18.

The irradiation container 18 is then loaded into the treatment chamber of an irradiation device, where the container 18 is then irradiated to provide an effective dose of light energy to the diluted buffy coat.

After irradiation, the treated buffy coat may either be directly reinfused to the patient, in which case the irradiation container may be detached from the remainder of the kit. Alternatively, the treated buffy coat may be recombined with the remaining plasma and packed red blood cells and then reinfused.

In a second aspect and with reference to FIGS. 2-16, a method is depicted for performing a low volume ECP procedure utilizing a syringe-like container, generally designated 50, that can be centrifuged, UVA treated, and then ready for injection into the patient. The depicted method shows the use of a single syringe-like container 50. However, as can be readily appreciated, multiple syringes 50 may be used to achieve the desired total volume of treated buffy coat.

The syringe 50 comprises a barrel 52 made of a UVA transparent material, such as glass or a cyclic-olefin polymer/copolymer. A needle 54 is removably attached to the syringe 50. A stopper 56 having a plunger handle 58 removably secured thereto is slidably received in the barrel 52.

Figure 2:
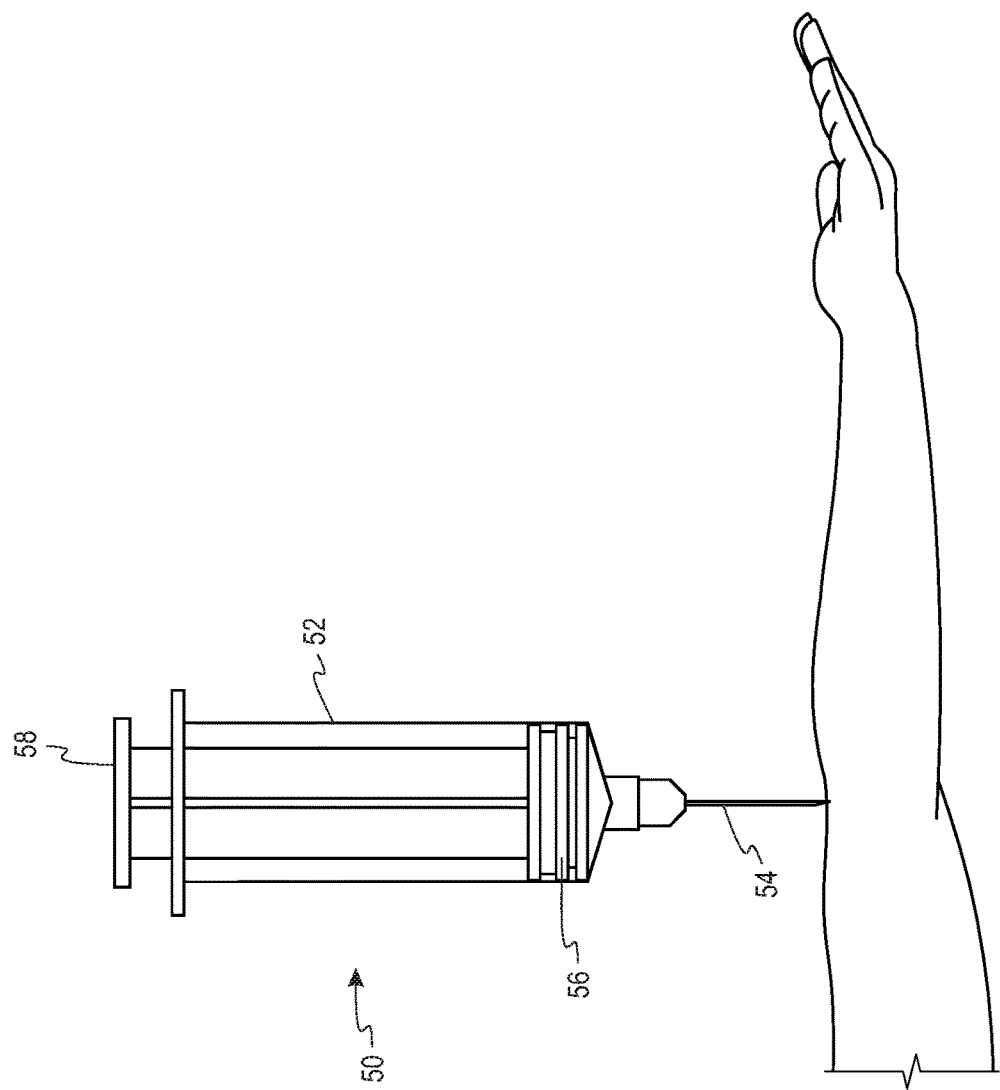
Figure 3:
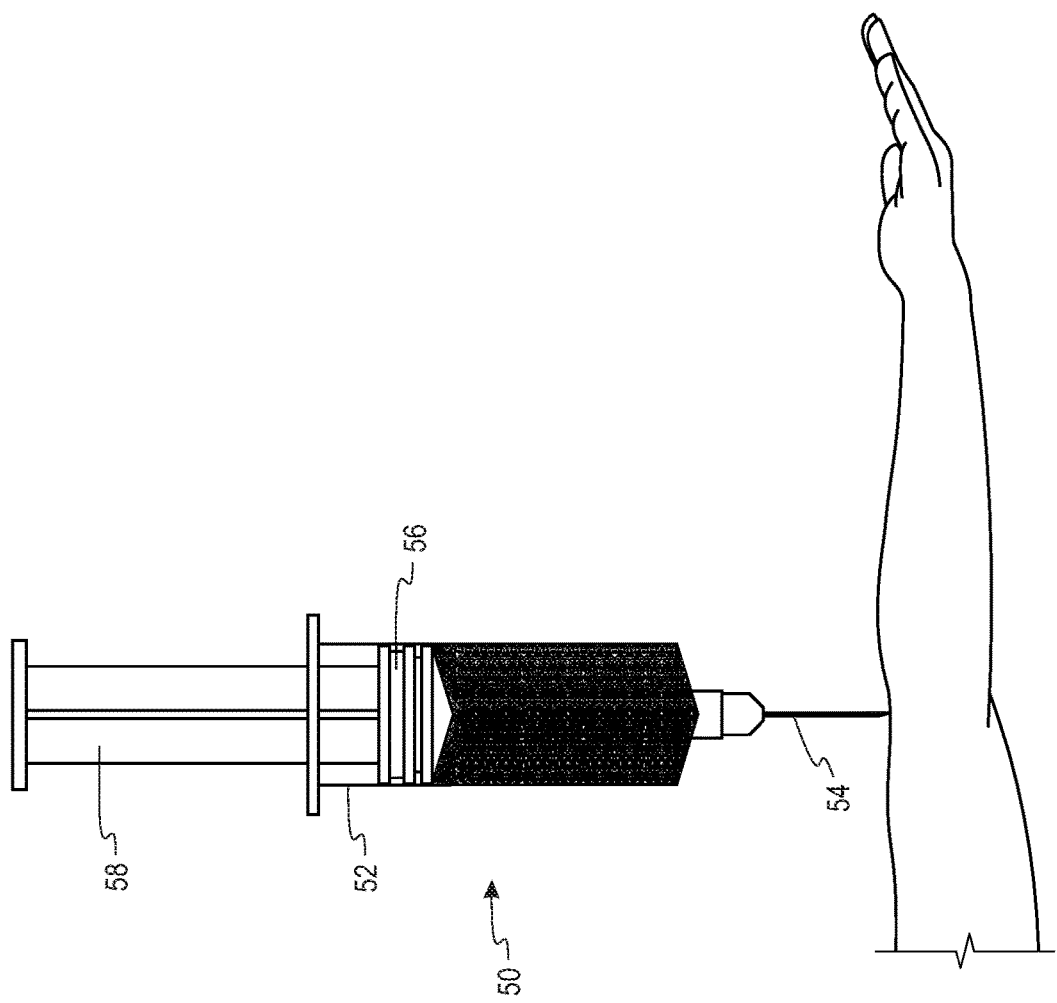

Initially, whole blood from the patient is manually drawn into the barrel 52 of the syringe 50 (FIGS. 2 and 3). The syringe may be pre-filled with the photoactivation agent (8-MOP). Alternatively, the photoactivation agent may be drawn into the syringe from a separate source at the start of the procedure either before or after the whole blood is drawn into the syringe. Alternatively, the photoactivation agent may be drawn into the syringe 50 after centrifugation (FIG. 7, described below) and prior to irradiation (FIG. 13, also described below).

Figure 5:
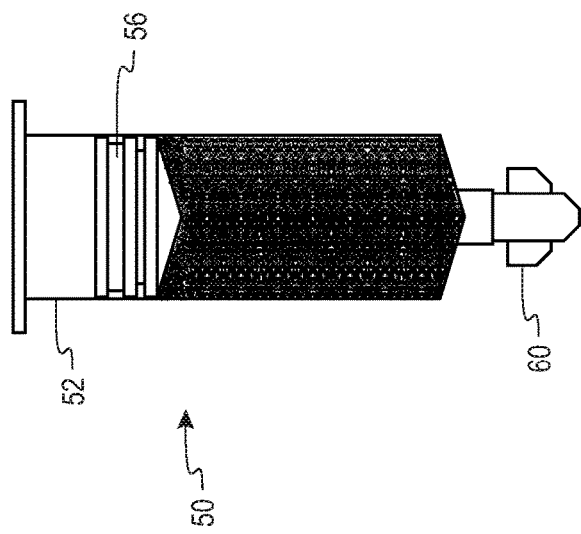
Figure 4:
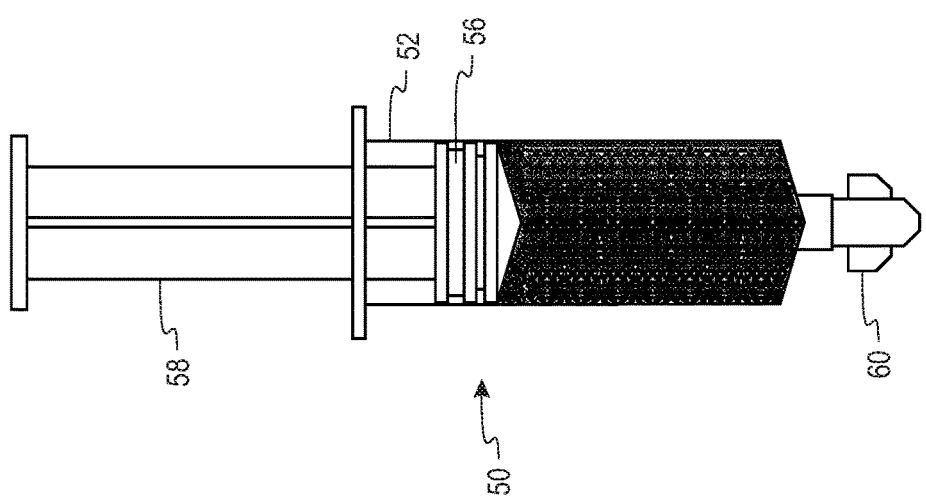
Figure 6:
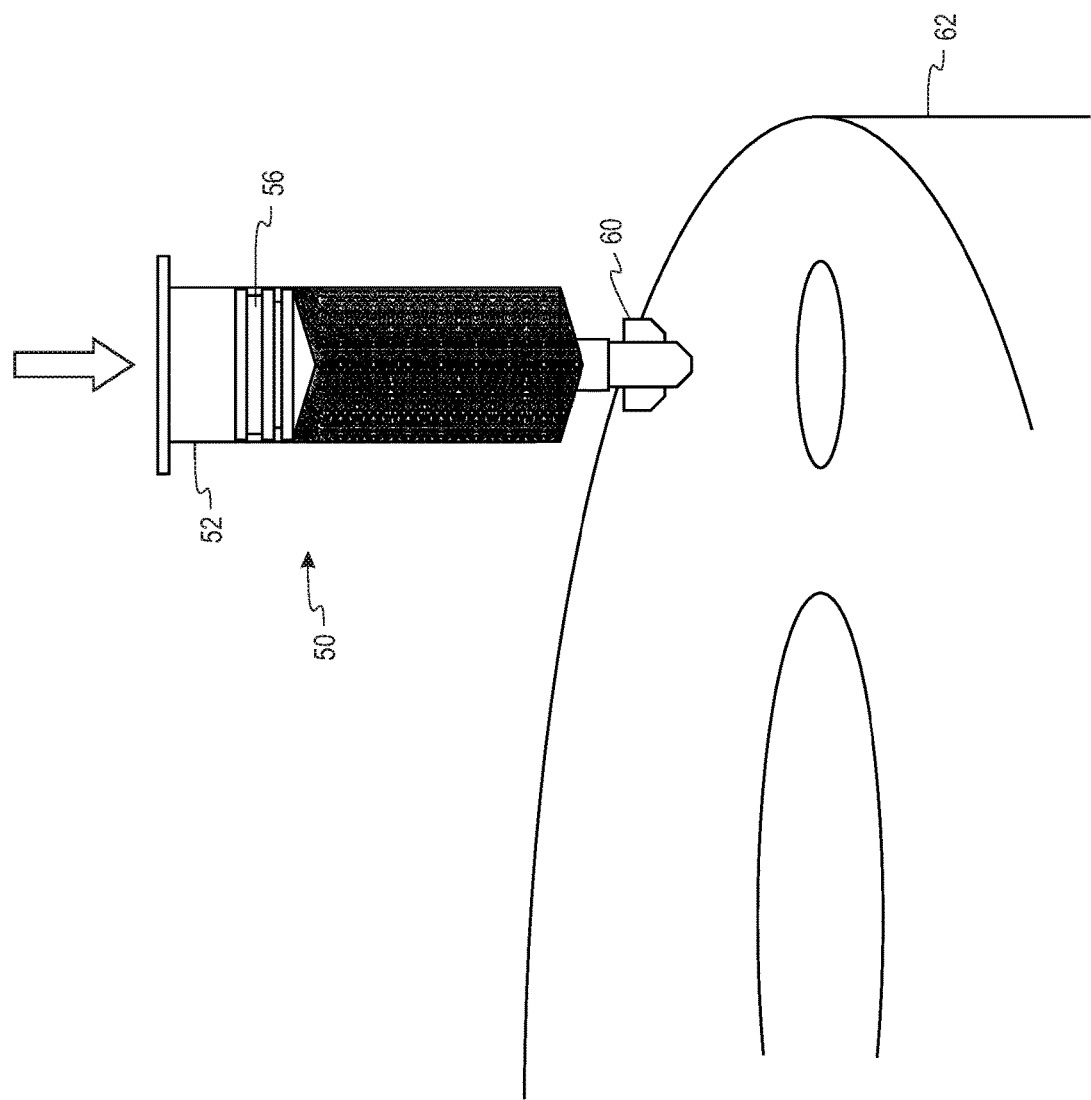
Figure 7:
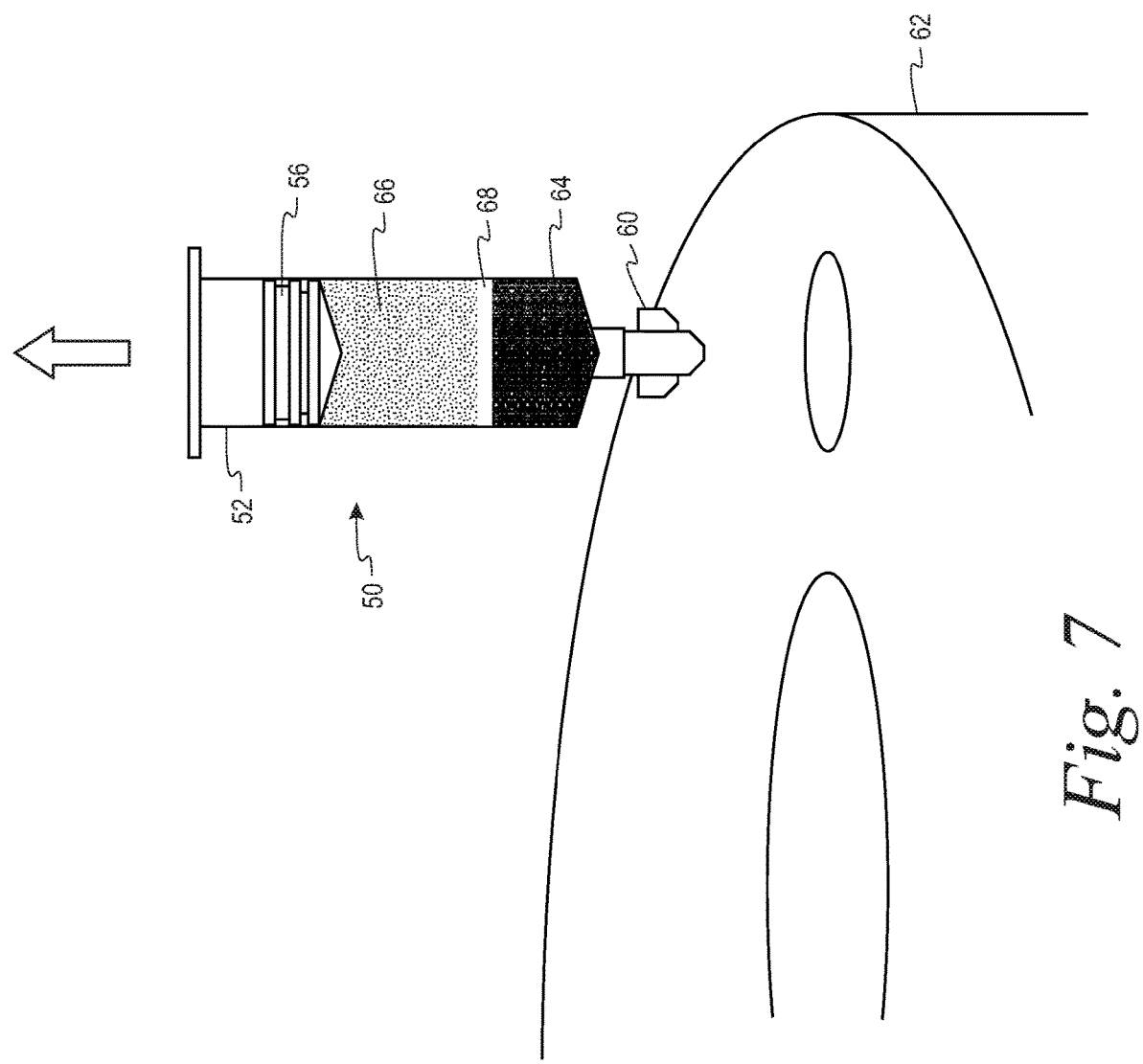

The needle 54 is then removed from the syringe 50 and replaced with a tip cap 60, and the plunger handle 58 removed (FIGS. 4 and 5). The syringe 50 is then placed in a centrifuge 62, which is then operated to spin the syringe 50 and separate the whole blood into layers comprising red blood cells 64, plasma 66 and buffy coat 68 (FIG. 7). The centrifuge 62 may be provided with a custom holder compatible with the standard centrifuge buckets for holding the syringe in the appropriate orientation.

The syringe 50 is then removed from the centrifuge 60 (FIG. 7), the plunger handle 58 reattached to the stopper 56 (FIG. 8), and the tip cap 60 removed. Care is to be taken in removing the tip cap 60 so as to not disturb the interface between the layers of red blood cells 64, buffy coat 68 and plasma 66. The syringe 50 is then connected to a return container 70 (FIG. 9). The layer of red blood cells 64 is evacuated into the return container 70 (FIG. 10) leaving only the buffy coat and plasma in the syringe.

The evacuation of the red blood cells may be done "manually," with the unaided vision of the operator being used to judge the position of the red blood cell-buffy coat interface in the syringe 50, or an optical sensor may be associated with the tubing segment connecting the return container to the syringe to determine when the interface exits the syringe.

Figure 11:
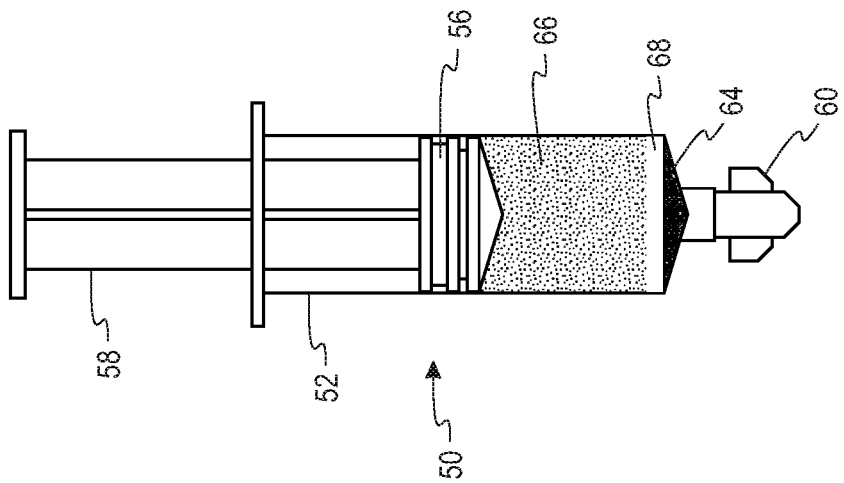
Figure 10:
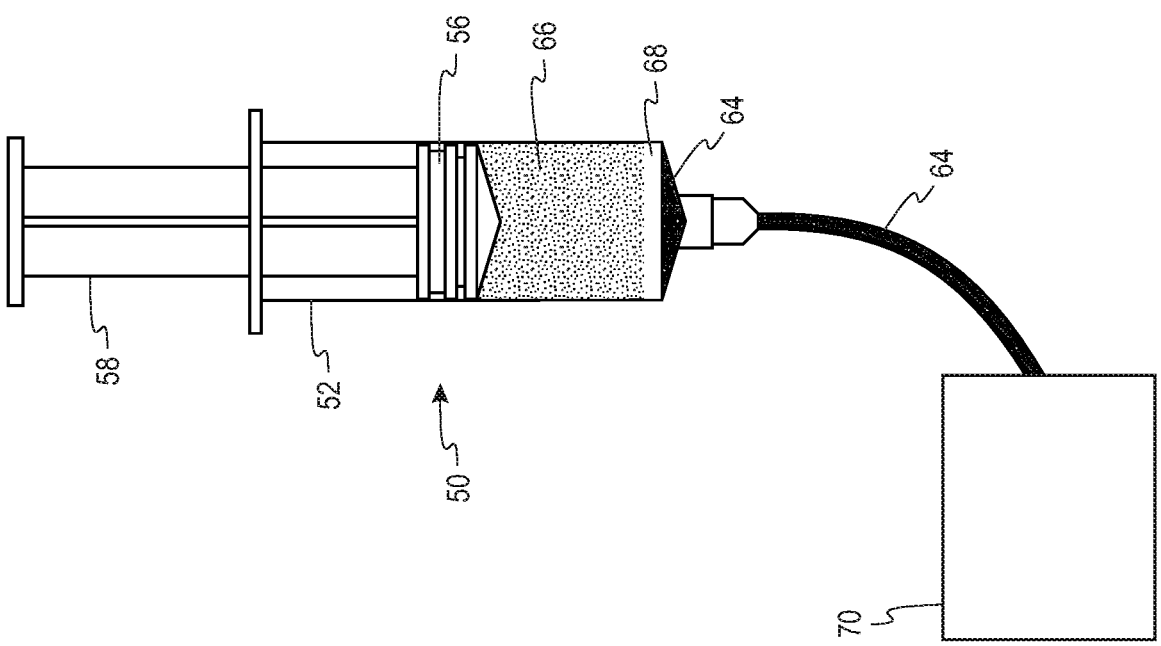

The return container is then detached from the syringe 50 and the tip cap 60 reattached (FIG. 11). The buffy coat and any residual red blood cells remaining in the syringe are then resuspended in the plasma (FIG. 12). It may be necessary to draw some additional diluent (such as saline) and/or some air into the syringe 50 to sufficiently dilute the buffy coat for irradiation. The resuspension may be performed manually by the operator simply shaking the syringe 50. Alternatively, the syringe 50 may be placed in a mechanical shaker to resuspend the buffy coat.

Figure 16:
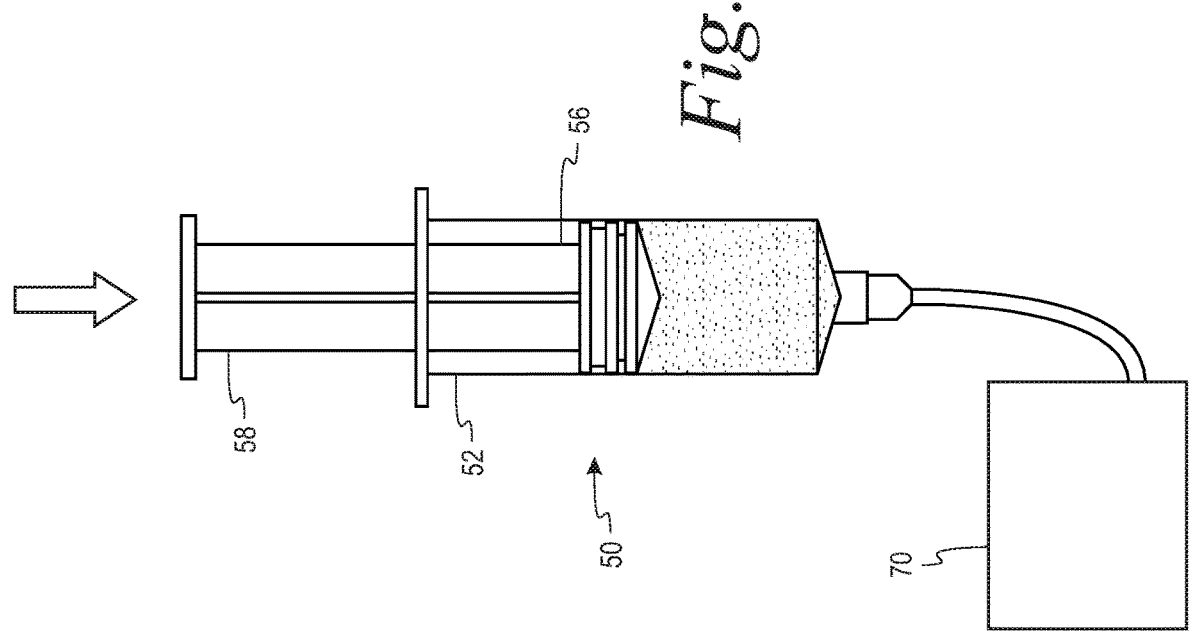
Figure 15:
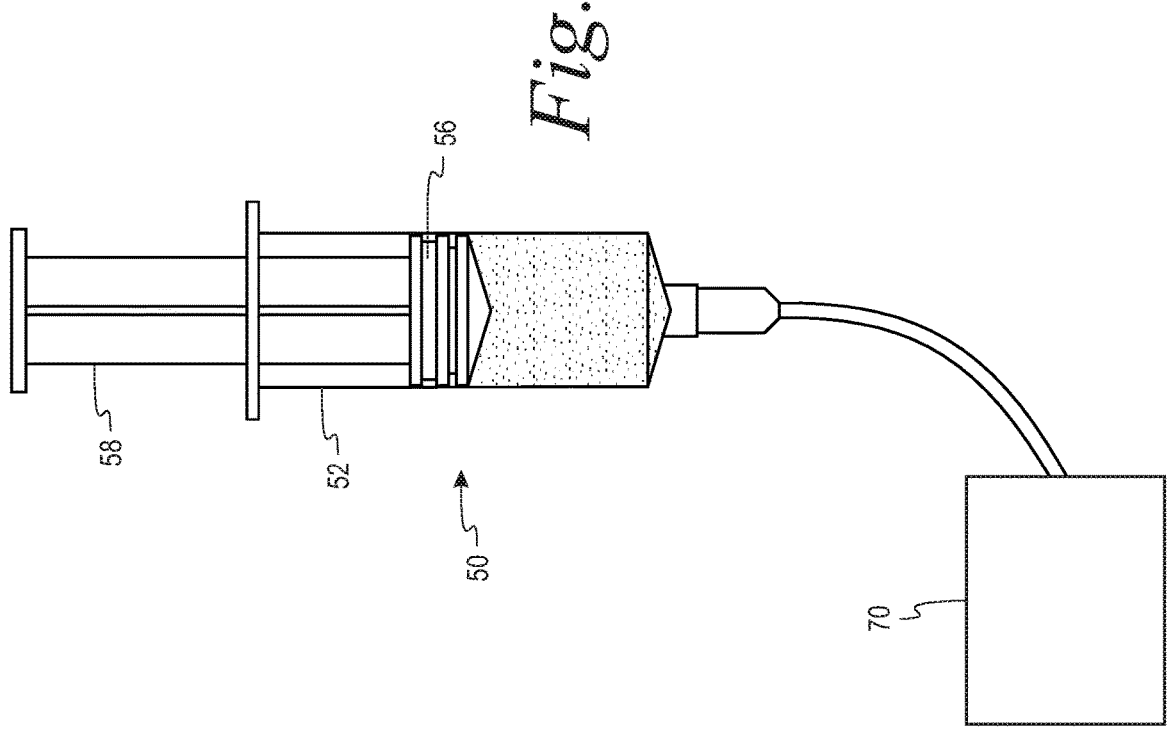

The syringe 50 is then placed in a UVA radiation device 72, where the syringe is subjected to a prescribed dose of UVA light to photoactivate the MNCs in the buffy coat and the 8-MOP (FIG. 13). After illumination, the syringe 50 is removed from the irradiation device (FIG. 14). The tip cap 60 is removed and the return container 70 reattached to the syringe 50 (FIG. 15). The entire contents of the syringe 50 are then dispensed into the return container 70, where it is recombined with the separated red blood cells (FIG. 16). The contents of the return container 70 may then be reinfused into the patient directly from the container 70. As can be appreciated, the process may be aided by the use of custom disposable tubing sets and/or automated syringes for syringe control.

Figure 17:
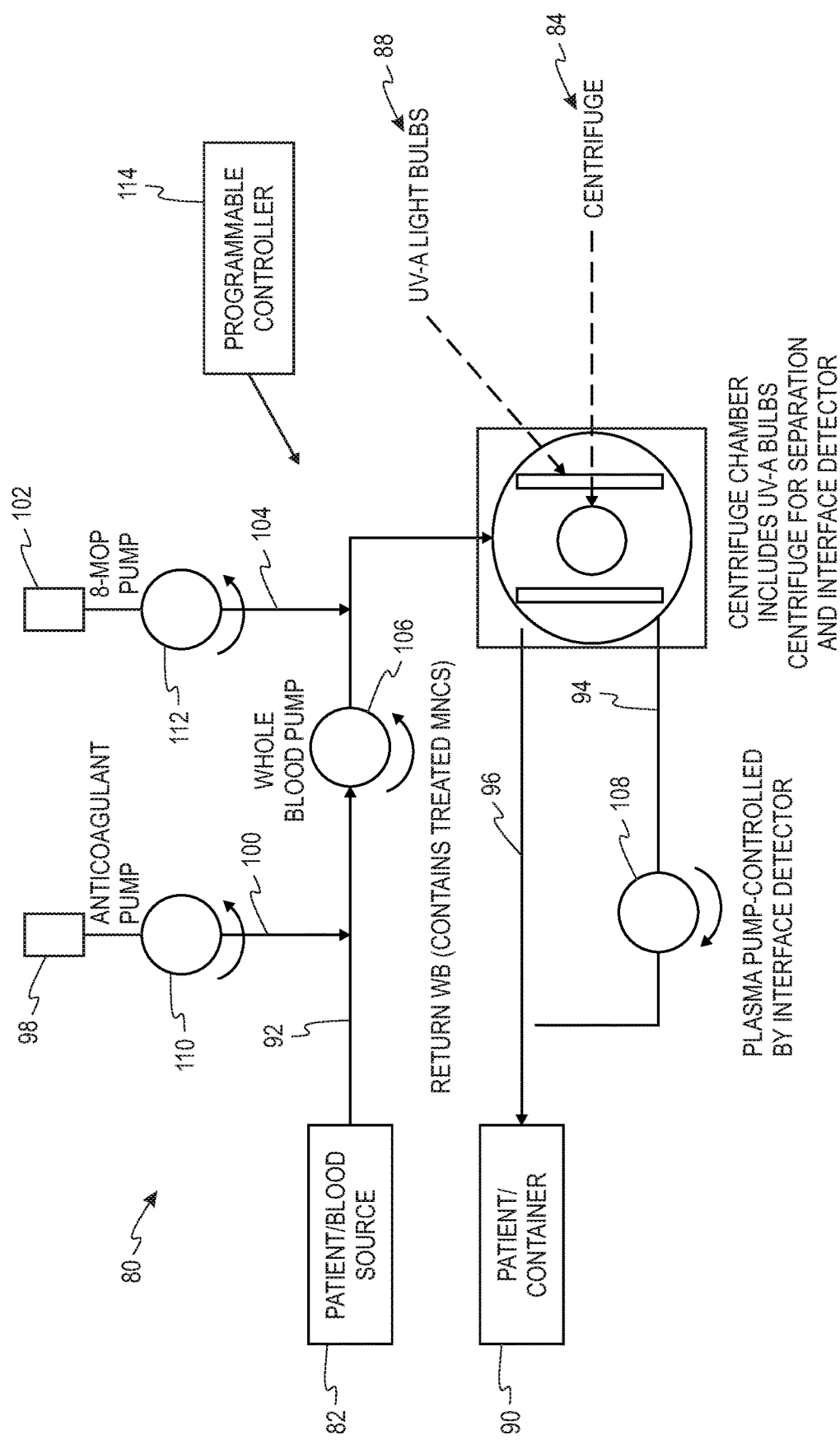
FIG. 17 is a schematic drawing of a third system and method for performing a low volume ECP procedure.

In a third aspect and with reference to FIG. 17, a system for performing low volume ECP generally designated 80 is disclosed in which the system 80 receives blood either directly from a patient or a container of previously collected blood, both of which are indicated by 82, adds 8-MOP in line, and sends it to a separation chamber that is positioned in a centrifuge 84. Upon centrifugation, the blood in the separation chamber separates into its components. A pump controls the level of plasma and red cells within the separation chamber by means of an interface detector within the centrifuge chamber, so that the level of red cells and plasma in the separation chamber is kept low. Consequently, the buffy coat layer is thin and takes up most of the volume in the separation chamber. When the optimal interface position is reached, UV-A lights 88 positioned within the centrifuge chamber are activated. Therefore, the MNCs will be treated in the centrifuge, and then can be immediately returned to the patient or to a separate container from which the treated MNCs will be reinfused to the patient, both of which are indicated by 90.

Returning to FIG. 17, the system includes a single-use disposable fluid flow circuit that is mounted on to a reusable hardware component. The fluid flow circuit comprises a separation chamber having a first tubing segment 92 connected thereto to provide fluid communication between the separation chamber and the patient or blood source 82, so that whole blood may be flowed through the first tubing segment 92 into the separation chamber. A second tubing segment 94 is in fluid communication with the separation chamber for flowing plasma and red blood cells that are separated from the whole blood from the separation chamber back to the patient or to a separate container 90. A third tubing segment 96 is in fluid communication with the separation chamber for flowing separated, UV-treated MNCs from the separation container and back to the patient or to the separate container 90. A container 98 holding anticoagulant is in fluid communication with the first tubing segment 92 through a fourth tubing segment 100 to add anticoagulant to the whole blood withdrawn from the patient or from the blood source 82 as it is flowing through the first tubing segment 92. Further, a container 102 holding a photoactivation agent is in fluid communication with the first tubing segment 92 through a fifth tubing segment 104 to add photoactivation agent in the appropriate volume to the contents of the separation chamber prior to irradiation.

The reusable hardware component comprises a housing within which a centrifuge is mounted. The centrifuge includes a UV-transmissive bowl in which the separator of the fluid flow circuit is mounted, and the UV-A emitting light source 88 configured to deliver UV-A light to the bowl of the centrifuge. An interface detector is provided configured to detect an interface between separated plasma, red blood cells and MNCs. The interface detector is mounted on the housing to be in association with the second tubing segment 94 of the fluid flow circuit.

Pumps 106, 108, 110 and 112 are respectively associated with each of the first, second, fourth and fifth tubing segments 92, 94, 100 and 104. The first pump 106 associated with the first tubing segment 92 flows whole blood from the patient or blood source 82 through the first tubing segment 92 and into the separation chamber. The second pump 108 is associated with the second tubing segment 94 for controlled removal of separated plasma and for flowing red blood cells from the separation chamber through the second tubing segment 94 and back to the patient or to the separate container for later reinfusion to the patient 90. The third pump 110 is associated with the fourth tubing segment 100 for flowing anticoagulant through the fourth tubing segment 100 and into the first tubing segment 92. The fourth pump 112 is associated with the fifth tubing segment 104 for flowing photoactivation agent through the fifth tubing segment 104 and into the first tubing segment 92.

The system also includes a programmable controller 114 that is programmed to automatically operate the first, second, third and fourth pumps, 106, 108, 110 and 112, the centrifuge 84, and the UV-A emitting light source 88. Further, the programmable controller may be programmed to control the operation of the second pump 108, based on a signal received from the interface detector.

In a fourth aspect and with reference to FIGS. 18-27, a system, generally designated 120, is illustrated comprising a single-use disposable kit and a reusable hardware component. The single-use kit includes a series of containers interconnected by tubing segments and an irradiation cartridge, while the hardware component at least one pump engaging one of the tubing segments for moving fluid through the kit, flow control devices, such as clamps, valves, pumps, associated with the tubing segments, an agitation device, for mixing the contents of one of the containers, an irradiation device including a UV light source configured to receive the irradiation cartridge, and a programmable controller to automatically operate the fluid flow control devices, the agitation device, and the irradiation device.

Figure 18:
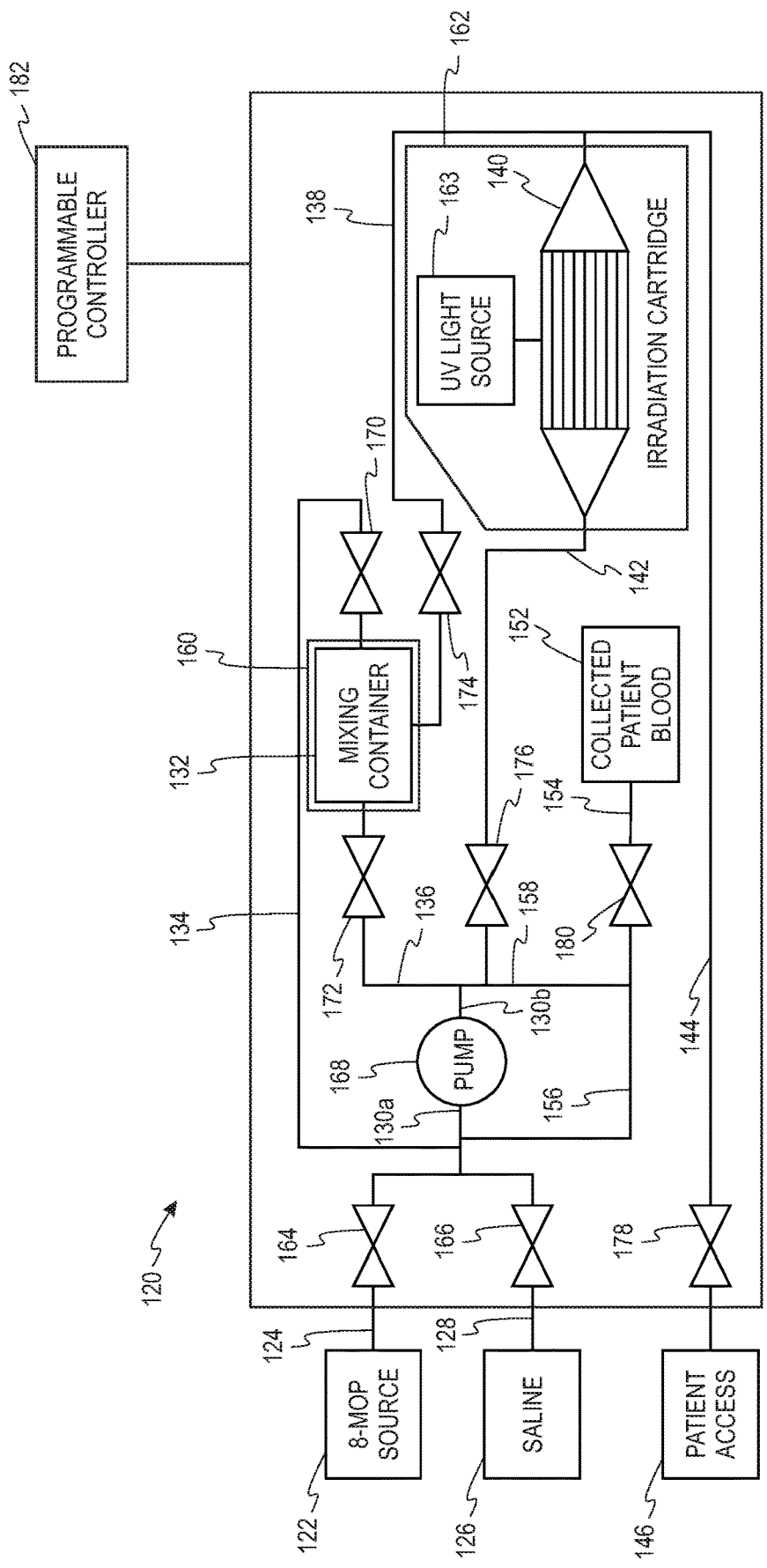
FIGS. 18-26 schematic views of a fourth system and method for performing a low volume ECP procedure.

More specifically, and with reference to FIG. 18, there is seen the combination of the single-use disposable kit and a reusable hardware component. The kit comprises a first container 122 holding a volume of photoactivation agent ("8-MOP Source") having a first tubing segment 124 connected thereto and a second container 126 holding a volume of saline having a second tubing segment 128 connected thereto, the first and second tubing segments merging together in a third tubing segment 130.

A mixing container 132 is provided that has fourth, fifth and sixth tubing segments 134, 136 and 138, respectively, connected thereto The fourth tubing segment 134 is connected to a first portion 130a of the third tubing segment 130, while the fifth tubing segment 136 is connected to a second portion 130b of the third tubing segment 130.

The sixth tubing segment 138 connects the mixing container 132 to an irradiation container or cartridge 140 that connects back to the second portion 130b of the third tubing segment 130 by a seventh tubing segment 142. An eighth tubing segment 144 is also connected to the irradiation container 140 through which the final product is flowed either to reinfuse directly to the patient through a patient access device 146, or to a treated product container 148 (FIG. 26) for reinfusion at a later time.

Figure 27:
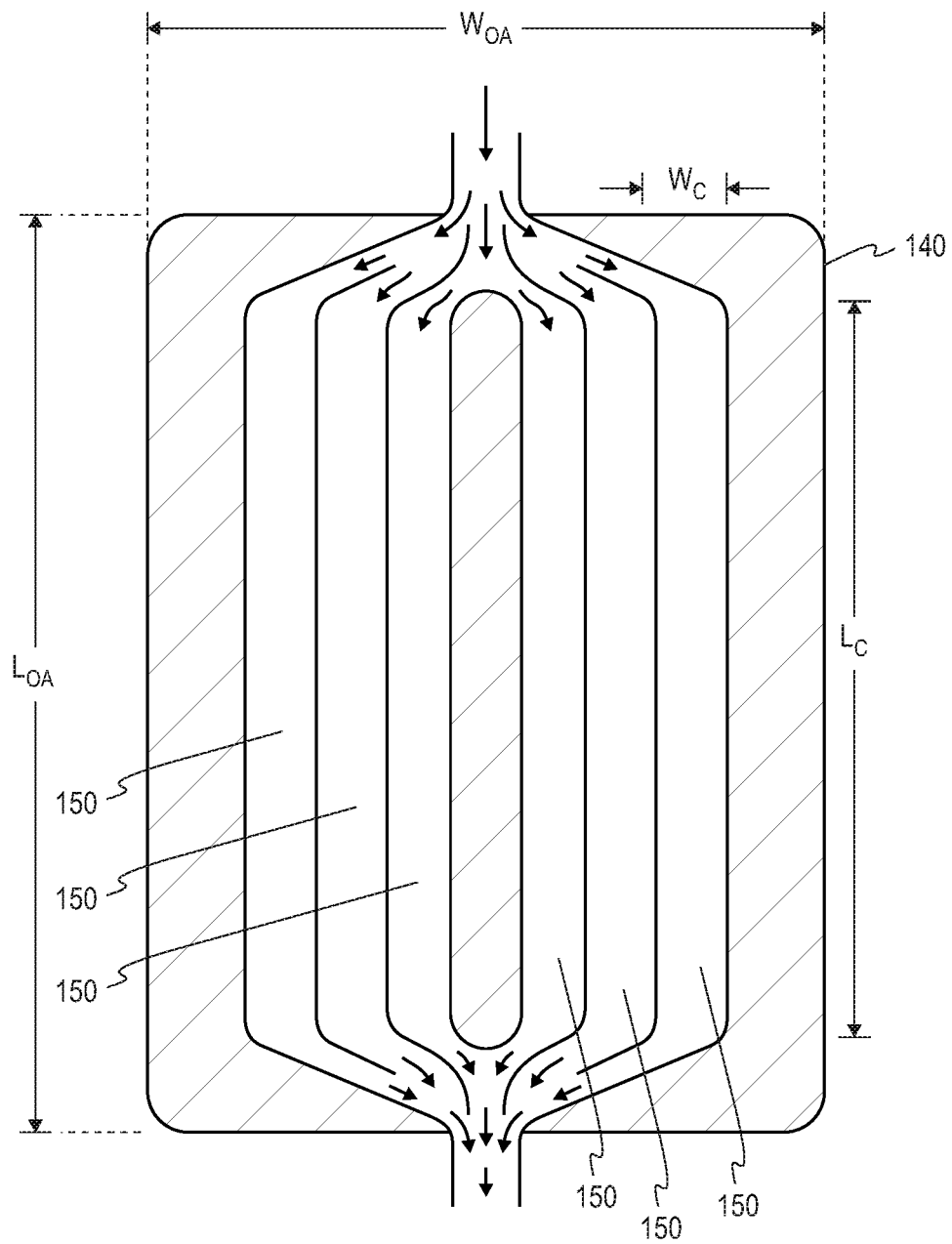
FIG. 27 is an enlarged view of an irradiation cartridge for use in the system and methods of FIGS. 18-26.
Figure 28:
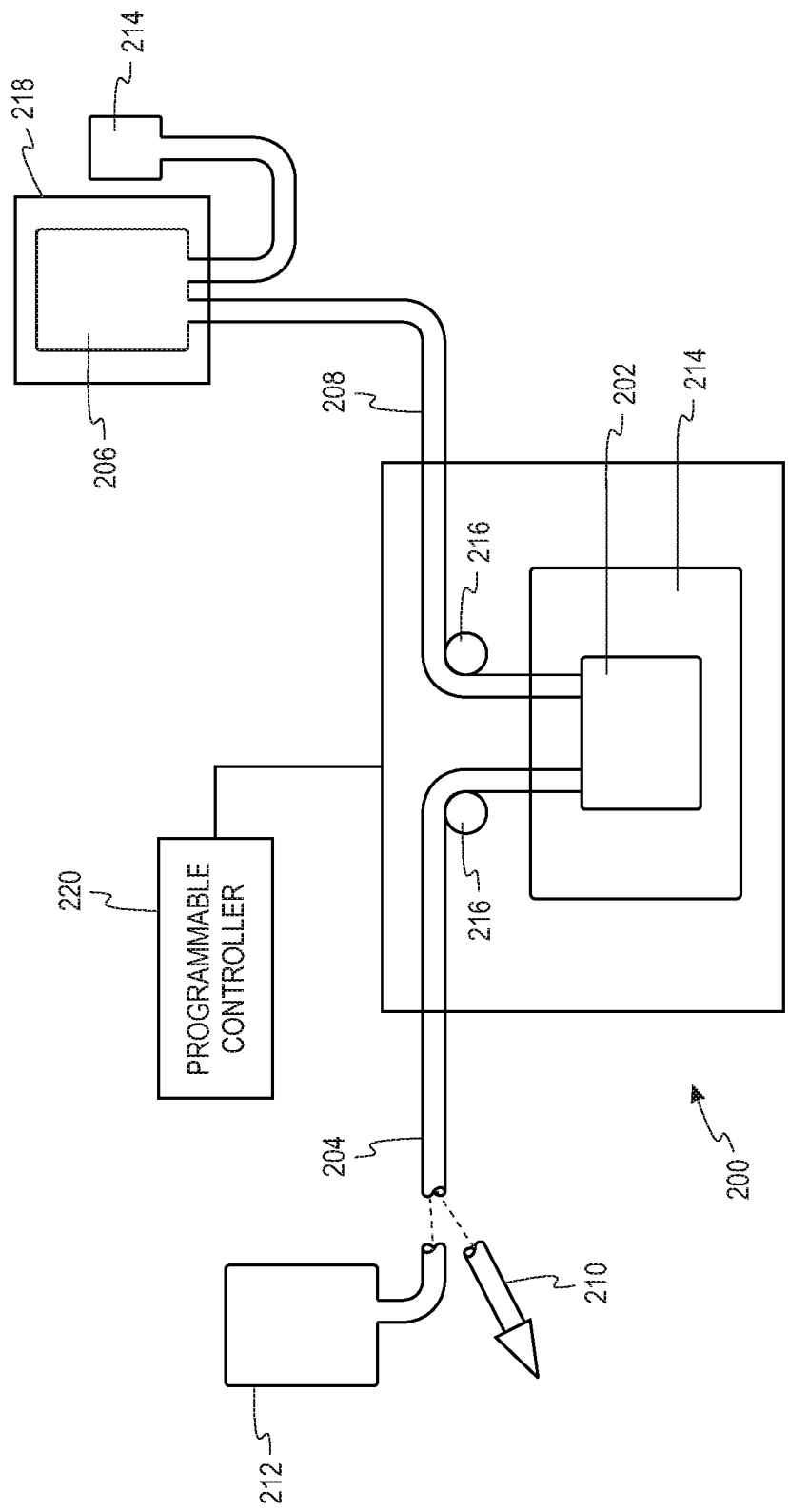
FIG. 28 is a schematic view of a fifth system and method for performing a low volume ECP procedure.

With reference to FIG. 27, the irradiation container 140 may have a fan-shaped configuration to enhance exposure of the blood to UV radiation as it flows through the cartridge. As illustrated, the cartridge divides the flow into six channels 150. By way of example, each channel may have a width $W_C$ of approximately 1.5 cm and a straight length $L_C$ of approximately 20 cm, with the overall dimensions of the cartridge being 15 cm in width, $W_{O4}$, and 28 cm in length, $L_{O4}$. The cartridge 140 has a fluid capacity of approximately 20 mL, and provides for a fluid thickness of approximately 1 mm on average.

Figure 26:
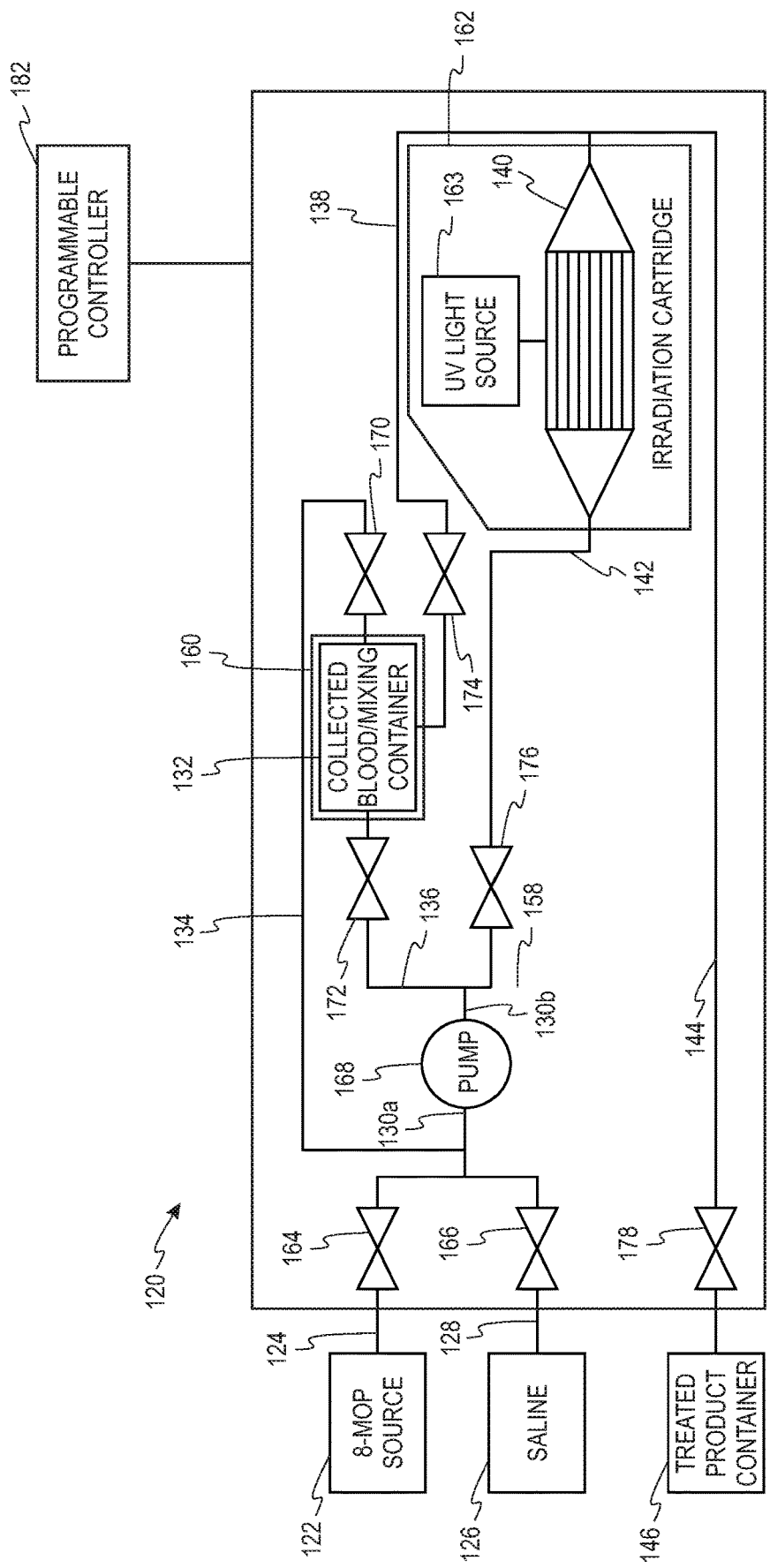

As shown in FIG. 18, the kit may include a separate container 152 of previously-collected whole blood having a ninth tubing segment 154 connected thereto through which flow is established with the first portion 130a of the third tubing segment 130 through a tenth tubing segment 156 and with the second portion 130b of the third tubing segment 130 through an eleventh tubing segment 158. Alternatively, mixing container 132 may be prefilled with anticoagulated whole blood, as shown in FIG. 26.

The reusable hardware component includes an agitation device 160 configured to receive the mixing container 132 and an irradiation device 162 having a UV light source 163 configured to receive the irradiation container 140. Flow control devices are associated with one or more of the first, second, third, fourth, fifth, sixth, seventh and eighth tubing segments. As illustrated, flow control devices 164, 166, 170, 172, 174,176, 178 and 180 associated with, respectively, the first, second, fourth, fifth, sixth, seventh, eighth and ninth tubing segments 124, 128, 134, 136, 138, 142, 144 and 154, comprise a valve or clamp, while the third fluid flow control 168 device is a pump interposed between the first and second portions 130a, 130b of the third tubing segment 130.

A programmable controller 182 automatically operates the fluid flow control devices, the agitation device, and the irradiation device in accordance with an algorithm that provides for optimal dilution of the whole blood needed to achieve the target UVA dose.

Figure 19:
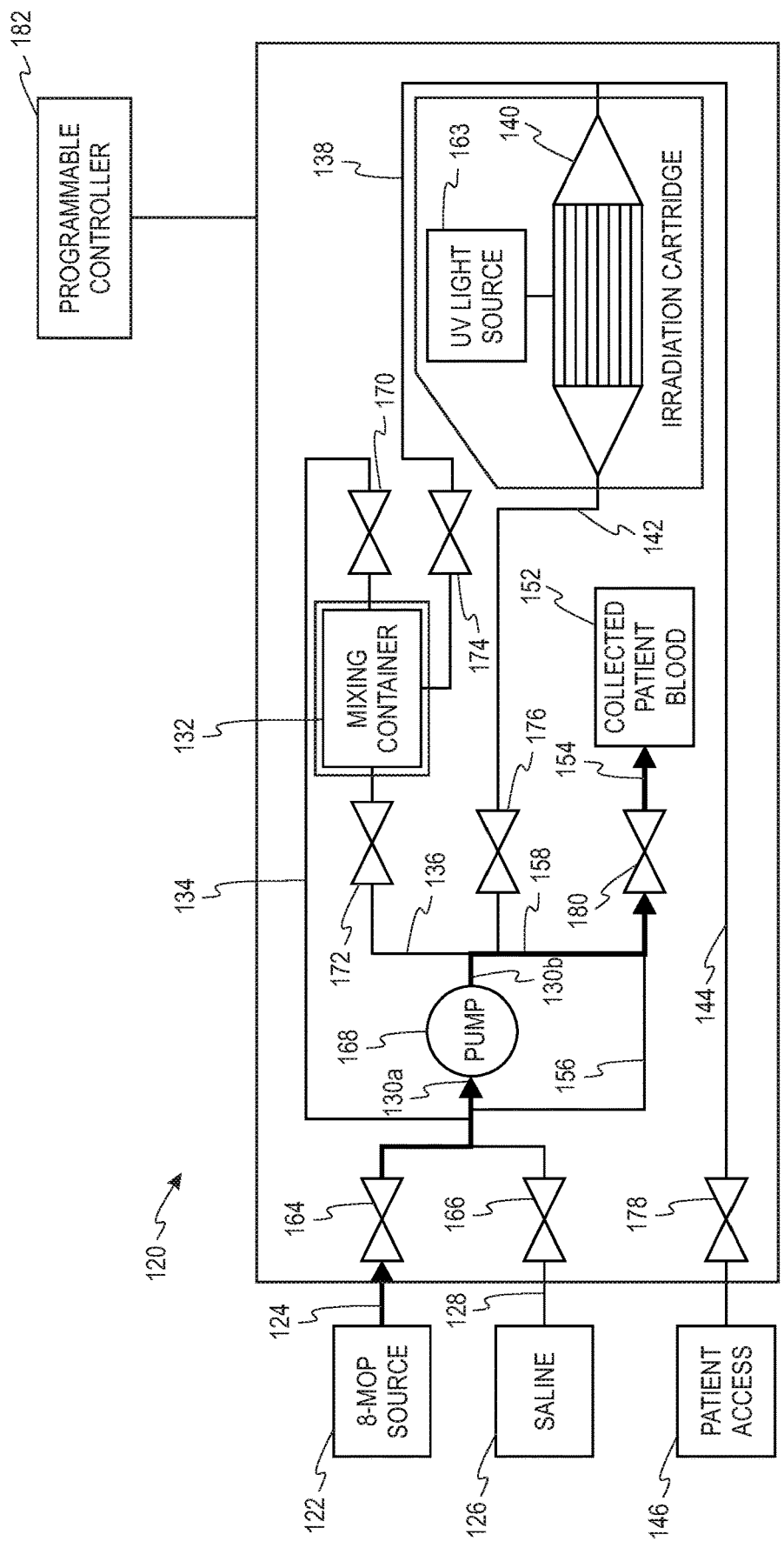
Figure 20:
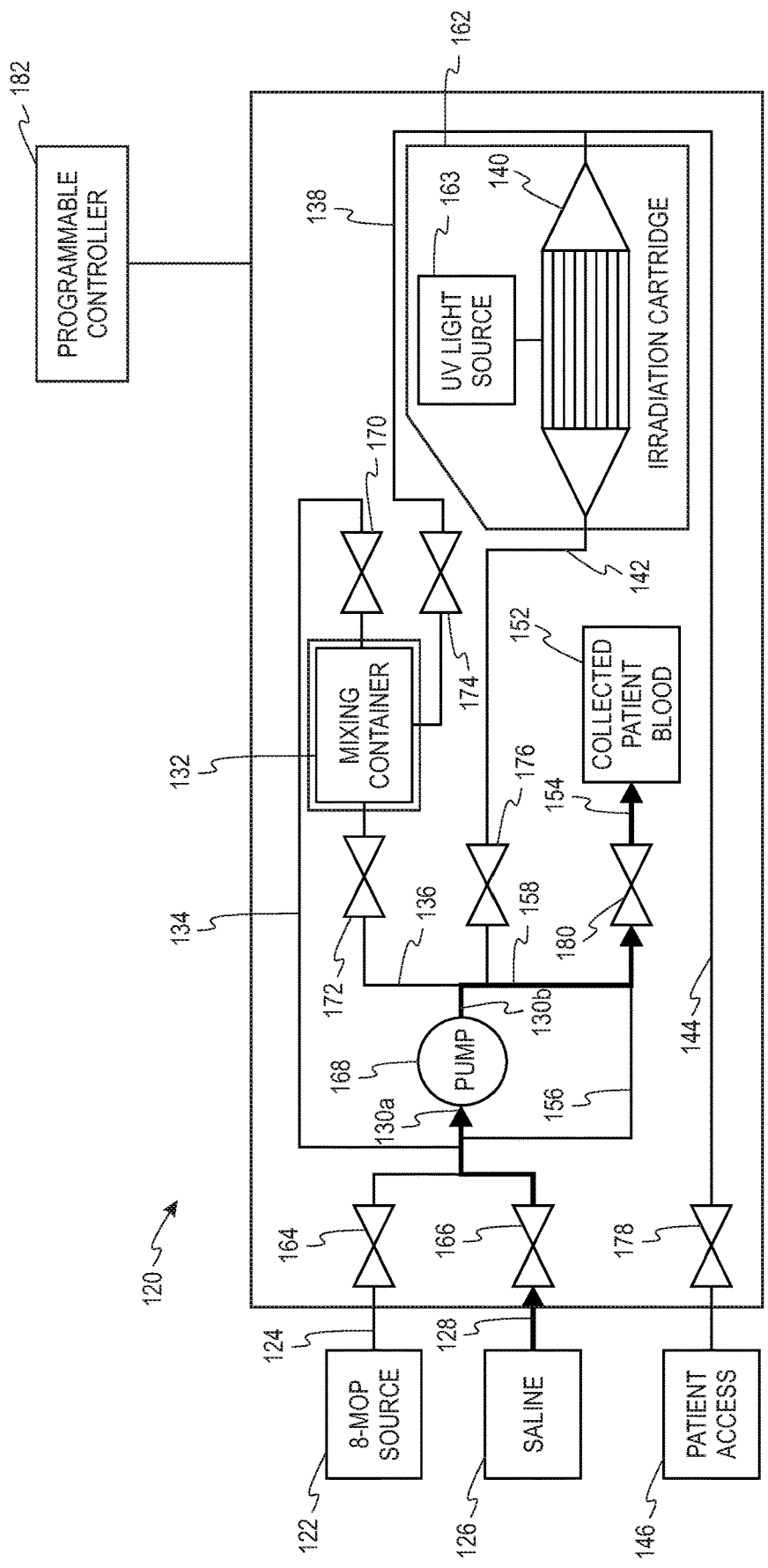

The use of the system of 18 is illustrated in FIGS. 19-25. With reference to FIG. 19, photoactivation agent is flowed from the first container 122 by means of the pump 168 though the various tubing segments and flow control devices and into the container of previously-collected whole blood 152. Then, with reference to FIG. 20, saline is flowed form the second container 126 by means of the pump 168 through the various tubing segments and flow control devices and into the container of previously-collected whole blood 152 to dilute the whole blood.

Figure 21:
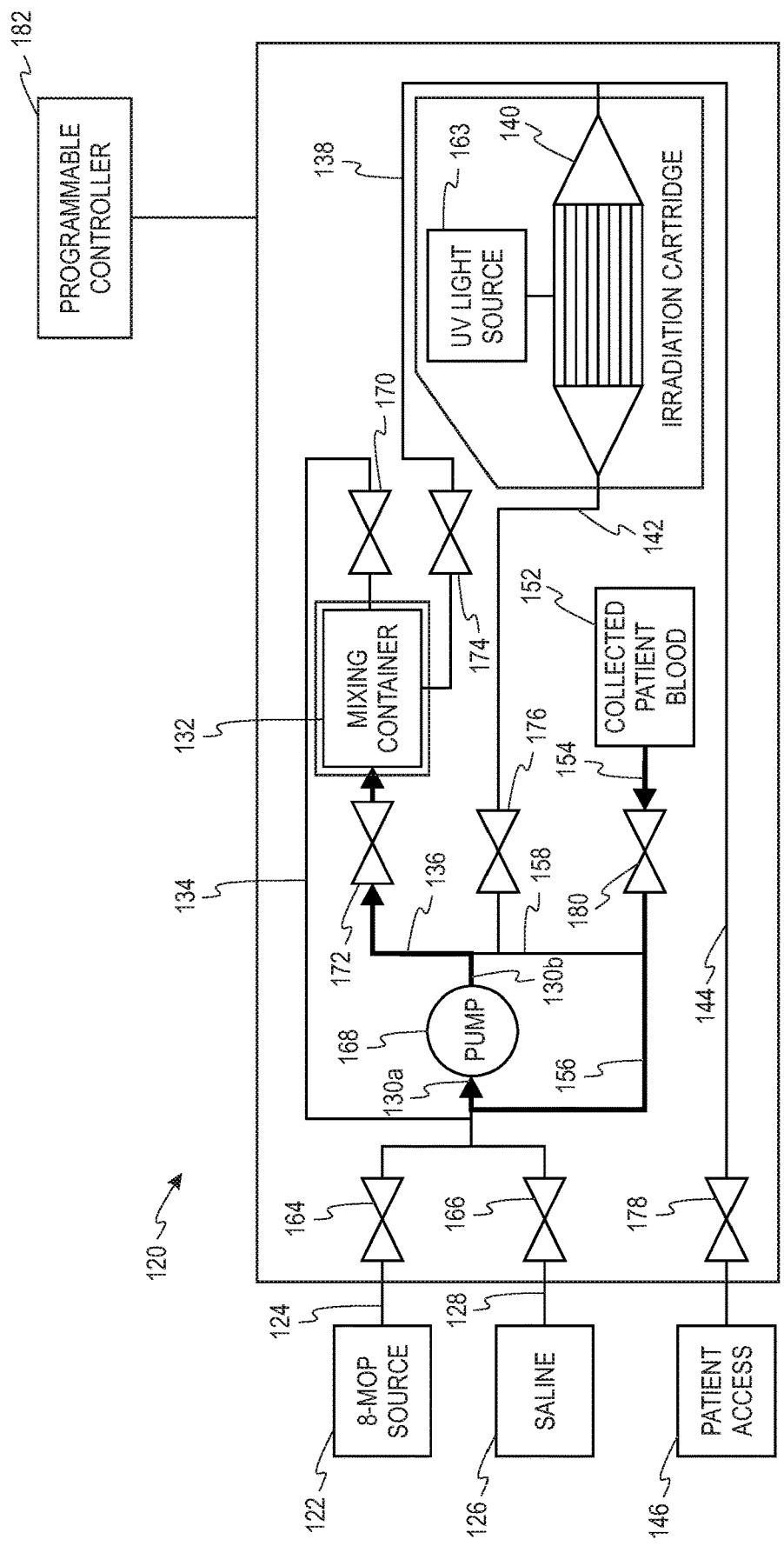
Figure 22:
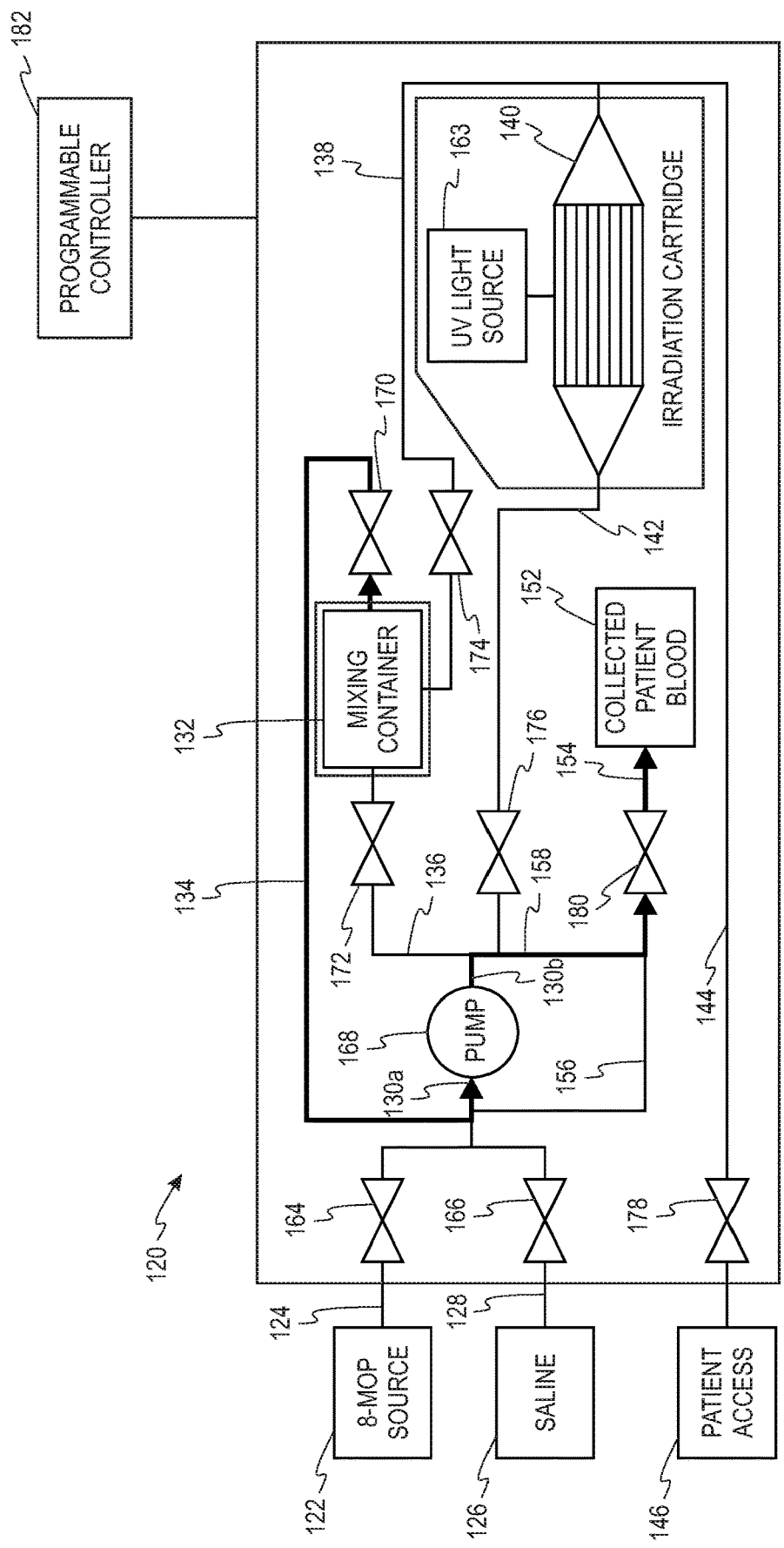

Then, with reference to FIG. 21, the contents of the container of the previously-collected whole blood 152 are flowed by means of the pump 168 through the various tubing segments and into the mixing container 132. The agitation device 160 is then activated to oscillate or otherwise move the mixing container 132 to mix the whole blood, photoactivation agent, and saline together.

Figure 23:
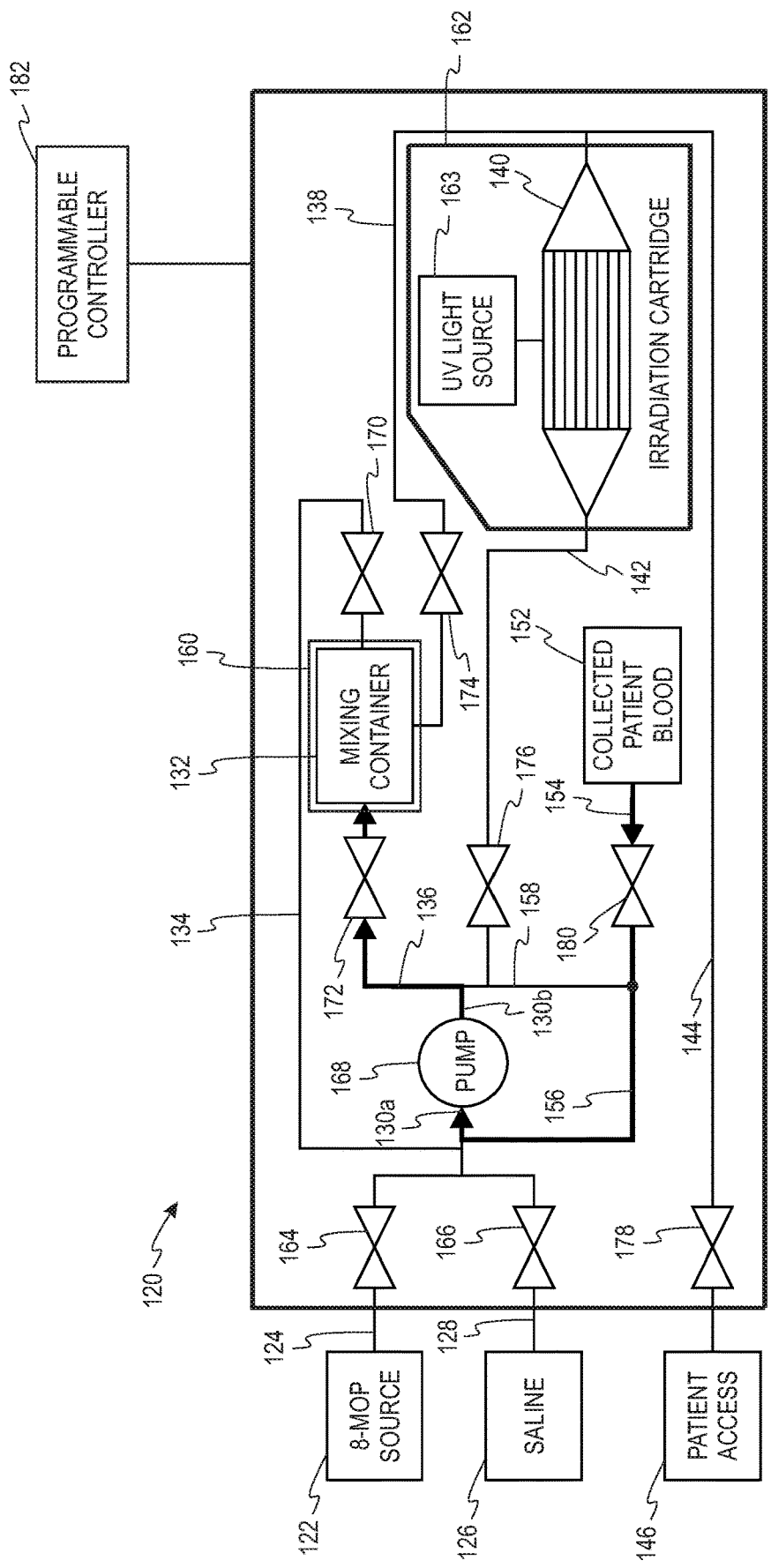
Figure 24:
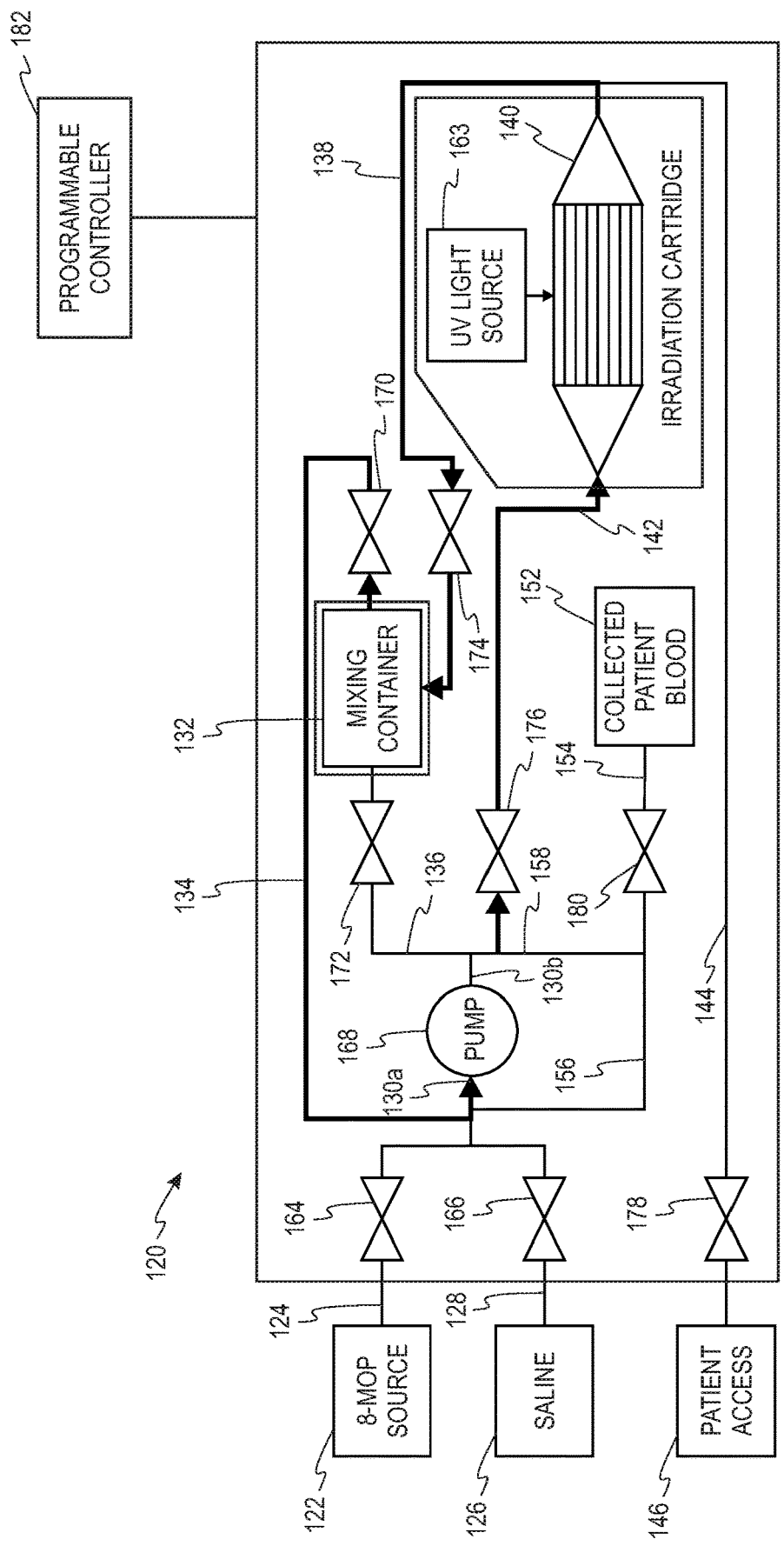
Figure 25:
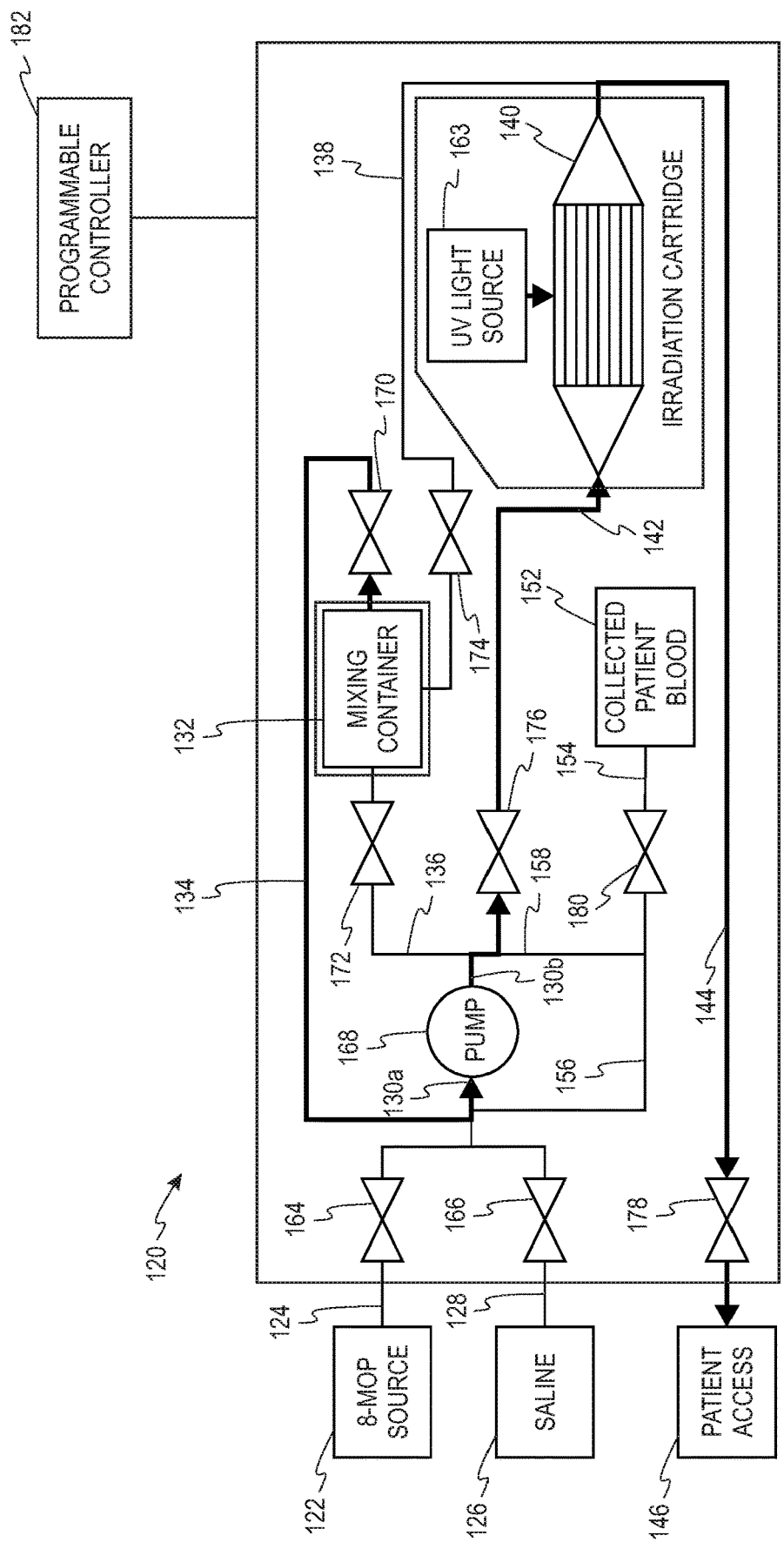

The contents of the mixing container 132 are then returned to the container 152 that originally held the previously collected whole blood (FIG. 22) and then flowed back to the mixing container for further mixing (FIG. 23). The contents of the mixing container is then circulated through the irradiation container, with the UV light source activated, and back to the mixing container until the target light dose has been delivered (FIG. 24). The treated blood may then be directly reinfused to the patient (as shown in FIG. 25). Alternatively, the treated blood can be flowed into a treated product container 148 (such as that shown in FIG. 26) for later reinfusion to the patient.

In a fifth aspect, a further system for performing low volume extracorporeal photopheresis, generally designated 200, is provided comprising a durable, reusable hardware component and a single-use fluid flow circuit. The fluid flow circuit comprises a separation chamber 202 having a first tubing segment 204 connected thereto for flowing whole blood into the separation chamber and a collection container 206 in fluid communication with the separation chamber by a second tubing segment 208.

The first tubing segment 204 may also comprise a phlebotomy device 210, such as a needle, for flowing whole blood directly from a patient through the first tubing segment and into the separation chamber. Alternatively, the first tubing segment may include a sterile connector for connecting a container 212 of previously collected whole blood to the first tubing segment 204. Optionally, a container 214 of photoactivation agent may be connected to the collection container 206 so that photoactivation agent may be introduced into the collection container 206. Further, the collection container 206 may be a syringe in order to facilitate reinfusion of the treated product into the patient.

The durable hardware component comprises a centrifuge 214 configured to receive the separation chamber 202 of the fluid flow circuit, and one or more pumps 216 for flowing whole blood through the first tubing segment 204 into the separation chamber 202 and for flowing buffy coat separated out of the whole blood by action of the centrifuge 214 through the second tubing segment 208 and into the collection container 206. As illustrated, a pump 216 is associated with each of the tubing segments 204, 208 for flowing fluid through the circuit. Alternatively, a single pump may be associated with either of the first and second tubing segments 204, 208.

The durable hardware component also includes an irradiation device 218 having a treatment chamber configured to receive the collection container 206 to deliver a prescribed dose of radiation to the contents of the collection container 206. A programmable controller 220 associated with the hardware component automatically controls the operation of the pump(s) 216, the centrifuge 214, and the irradiation device 218.

Thus, several different embodiments of systems and methods specifically developed for performing low volume ECP procedures have been disclosed, each of which eliminates the need for multiple kits and solutions and reduces some of the potential risks inherent in the use of such multiple kits and solutions. While specific embodiments have been described and depicted, the scope of the application is set forth in the following claims.

The invention claimed is:

1. A unitary disposable kit for performing low volume extracorporeal photopheresis comprising:
    a) a first container configured to receive whole blood from a patient and to be mountable in both a centrifuge and a blood component separator;
    b) a second container connected to the upper portion of the first container by a first tubing segment for receipt of plasma configured to be mountable in both the centrifuge and the blood component separator, the first container and second container each having an upper portion and a lower portion when mounted in the centrifuge and blood component separator;
    c) a third container connected to the lower end of the first container by a second tubing segment for receipt of packed red blood cells;
    d) a fourth container connected to the first container by a third tubing segment for receipt of buffy coat and configured to be mountable in an irradiation device.

2. The unitary disposable kit of claim 1 further comprising a phlebotomy needle connected to the first container by a fourth tubing segment for introducing whole blood into the first container and wherein the first container is prefilled with a volume of anticoagulant.

3. The unitary disposable kit of claim 1 further comprising a fifth tubing segment connected to the fourth container for introducing a photoactivation agent into the fourth container.

4. The unitary disposable kit of claim 3 further comprising a fifth container containing prefilled with a volume of photoactivation agent and connected to the fourth container by the fifth tubing segment.

5. The unitary disposable kit of claim 3 further comprising an in-line anti-microbial filter associated with the fifth tubing segment.

6. The unitary disposable kit of claim 1 further comprising a sixth container prefilled with a volume of saline and connected to the first container by a sixth tubing segment for introducing saline into the first container.

7. The unitary disposable kit of claim 1 wherein a flow control clamp is associated with at least one of the tubing segments.

8. The unitary disposable kit of claim 1 wherein a break-away cannula is associated with at least one of the tubing segments.

9. The unitary disposable kit of claim 1 wherein the third container is prefilled with a volume of allogenic, ABO packed red blood cells matched to the patient.

10. A method for performing a low volume extracorporeal photopheresis procedure utilizing the unitary disposable kit of claim 1 in combination with centrifuge, the blood separation device and the irradiation device, comprising:
    a) mounting the first container containing a volume of whole blood in the centrifuge;
    b) operating the centrifuge to separate the whole blood into separate layers of plasma at the upper end of the first container, packed red blood cells at the lower end of the first container, and buffy coat intermediate the layers of plasma and packed red blood cells;
    c) loading the first container onto the blood separation device;
    d) expressing plasma from the upper end of the first container through the first tubing segment and into the second container;
    e) expressing packed red blood cells from the lower end of the first container through the second tubing segment and into the third container;
    f) retaining the buffy coat in the first container;
    g) adding plasma from the second container and/or saline to the first container to dilute the buffy coat retained in the first container and to achieve a target hematocrit and volume for the diluted buffy coat;
    h) flowing the diluted buffy coat through the third tubing segment and into the fourth container;
    i) adding photoactivation agent to the diluted buffy coat;
    j) loading the fourth container onto the irradiation device;
    k) irradiating the fourth container.

11. The method of claim 10 wherein photoactivation agent is added to the diluted buffy coat by flowing photoactivation agent from the fifth container through the fifth tubing segment and into the fourth container.

12. The method of claim 10 wherein photoactivation agent is added to the diluted buffy coat by introducing photoactivation agent into the third tubing segment simultaneously with flowing the diluted buffy coat through the third tubing segment and into the fourth container.

13. The method of claim 10 wherein the buffy coat is diluted by flowing saline from the sixth container through the sixth tubing segment and into the first container.

14. The method of claim 10 wherein the irradiated buffy coat is recombined with a portion of the separated plasma and/or packed red blood cells.

15. The method of claim 10 wherein any excess air in the fourth container is flowed into the first container prior to irradiation of the fourth container.

16. The method of claim 10 wherein the irradiated buffy coat is reinfused into the patient.

17. The method of claim 10 wherein a label identifying the patient is applied to at least the fourth container prior to collecting whole blood in the first container and separating the fourth container from the unitary kit only after the diluted buffy coat is flowed from the first container into the fourth container.

18. The method of claim 10 wherein a label identifying the patient is applied to at least the fourth container prior to collecting whole blood in the first container and separating the fourth container from the unitary kit only after the fourth container is irradiated.

19. The unitary disposable kit of claim 1 wherein each of the first, second, third, and fourth containers is configured to be mountable in the centrifuge.

20. A system for performing low volume extracorporeal photopheresis comprising a single-use fluid flow circuit and a durable hardware component, the single-use fluid flow circuit comprising a separation chamber configured to be received in a centrifuge, a first tubing segment connected to the separation chamber for flowing whole blood thereto, a collection container for receipt of buffy coat separated from the whole blood in the separation chamber by operation of the centrifuge and configured to be received in a treatment chamber of an irradiation device, and a second tubing segment for flowing buffy coat from the separation chamber onto the collection container, the durable hardware component further comprising the centrifuge configured to receive the separation chamber of the fluid flow circuit; one or more pumps for flowing whole blood through the first tubing segment to the separation chamber and flowing buffy coat through the second tubing segment into the collection container; an irradiation device having a treatment chamber configured to receive the collection container, and a programmable controller for automatically operating the one or more pumps, the centrifuge and the irradiation device.

21. The system of claim 20 wherein the fluid flow circuit further comprises a container of photoactivation agent connected to the collection container.

22. The system of claim 20 wherein the collection container comprises a syringe.

23. The system of claim 20 in which the first tubing segment comprises one of a phlebotomy device for flowing whole blood directly from a patient through the first tubing segment and to the separation chamber and a sterile connector for connecting a container of previously-collected whole blood to the first tubing segment.

24. The system of claim 20 wherein the one or more pumps are associated with each of the first and second tubing segments.

* * * * *